US007138242B2

(12) United States Patent
Reed et al.

(10) Patent No.: US 7,138,242 B2
(45) Date of Patent: Nov. 21, 2006

(54) OLFACTORY RECEPTOR EXPRESSION LIBRARIES AND METHODS OF MAKING AND USING THEM

(75) Inventors: Randall R. Reed, Baltimore, MD (US); King-Wai Yau, Towson, MD (US); Dietmar Krautwurst, Bergholz Rebhrucke (DE)

(73) Assignee: Johns Hopkins University, Baltimore, MD (US)

( * ) Notice: Subject to any disclaimer, the term of this patent is extended or adjusted under 35 U.S.C. 154(b) by 284 days.

(21) Appl. No.: 10/259,423

(22) Filed: Sep. 30, 2002

(65) Prior Publication Data

US 2003/0175744 A1 Sep. 18, 2003

Related U.S. Application Data

(62) Division of application No. 09/465,901, filed on Dec. 17, 1999, now Pat. No. 6,492,143.

(60) Provisional application No. 60/112,605, filed on Dec. 17, 1998.

(51) Int. Cl.
*G01N 33/53* (2006.01)
(52) U.S. Cl. .......................... 435/7.1; 435/4; 435/7.21
(58) Field of Classification Search .................. 435/7.1
See application file for complete search history.

(56) References Cited

U.S. PATENT DOCUMENTS

| 5,683,912 A | 11/1997 | Elgoyhen | 435/252.3 |
|---|---|---|---|
| 5,869,266 A | 2/1999 | Wolozin | 435/7.21 |
| 5,948,890 A | 9/1999 | Soppet | 530/350 |
| 5,955,281 A | 9/1999 | Brann | 435/6 |
| 5,993,778 A | 11/1999 | Firestein | 424/9.1 |
| 6,013,766 A | 1/2000 | Elgoyhen | 530/350 |

OTHER PUBLICATIONS

Singer et al., "Molecular Modeling of Ligand Receptor Interactions in the Ors Olfactory Receptor", *Neuroreport*, (1994), pp. 1297-1300, vol. 5, No. 10.
Buiakova, et al., "Olfactory Maker Protein (OMP) Gene Deletion Causes Altered Physiological Activity . . . ", *Proceeding of the National Academy of Sciences of the United States of America*, (1996), pp. 9858-9863, vol. 93, No. 18.
Heymann, et al., "Expression, Stability, and Membrane Integration of Truncation Mutants . . . ", *Proceedings of the National Academy of Sciences of the United States of America*, (1997), pp. 4966-4971, vol. 94, N.10.
Barry, et al., "An Analysis of Odorant-Induced Currents in On-Cell Patches on Mammalian Olfactory Receptor Neurons", *Annals of the New York Academy of Sciences*, (1998), pp. 208-211, vol. 855, Nov. 30.
Zehntner, "Differentiation in an Olfactory Cell Line", *Annals of the New York Academy of Sciences*, (1998), pp. 235-239, vol. 855, Nov. 30.

Pelosi, "Odorant Binding Proteins: Structural Aspects", *Annals of the New York Academy of Sciences*, (1998), pp. 281-293, vol. 855, Nov. 30.
Hua Zi-Chun, "CDNA Cloning and Heterologous Expression of Mouse CYP2G1", *Annals of the New York Academy of Sciences*, (1998), pp. 309-312, vol. 864, Dec. 13.
Qasba, et al., "Tissue and Zonal Specific Expression of an Olfactory Receptor Transgene", *The Journal of Neuroscience: The Official Journal of the Society for Neuroscience*, (1988), pp. 227-236, vol. 18, No. 1 Jan.
Zhao, et al., "Functional Expression of a Mammalian Odorant Receptor", *Science*, (1998). pp. 279, (5348), Jan. 9.
Kudrycki, et al., "Effects of Mutation of the OLF-A Motif on Transgene Expression . . . ", *Journal of Neuroscience Research*, (1998), pp. 159-172, vol. 52, Apr.
Moro, et al., "Human P2Y Receptor Molecular Modeling and Site Directed Mutagenesis . . . ", *Journal of Medicinal Chemistry*, (1992), pp. 1456-1466., vol. 41, Apr.
Breer, et al., "Expression and Functional Analysis of Olfactory Receptors", *Annals of the New York Academy of Sciences*, (1998), pp. 175-181, vol. 855, Nov. 30.
Singer, et al., "Potential Ligand Binding Residues in Rat Olfactory Receptors . . . ", *Receptors & Channels*, (1995), pp. 89-95, vol. 3, No. 2.
Pelosi, "Odorant Binding Proteins", *Critical Reviews in Biochemistry and Molecular Biology*, (1994), pp. 199-228, vol. 29, No. 3.
Parmentier, et al., La Famille Des Recepteurs Couples Aux Proteins G Et Ses Orphelins, *Medecine Sciences: M/S*, (1995), pp. 222-231, vol. 11, No. 2.
Krautwurst, et al., "Identification of Ligand For Olfactory Receptors by Functional Expression of a Receptor Library", *Cell*, (1998), pp. 917-926, vol. 95, No. 7, Dec. 23.
Kiefer, et al., "Expression of an Olfactory Receptor in *Escherichia Coli* . . . ", *Biochemistry*, (1996), pp. 16077-16084, vol. 35, No. 50.
Buck, L., "Identification and Analysis of a Multigene Family Encoding Odorant Receptors", *Chemical Senses*, (1993), pp. 203-208, vol. 18, No. 2.
Lancet, et al., "Olfaction from Signal Transduction and Termination to Human Genome Mapping", *Chemical Senses*, (1993), pp. 217-225, vol. 18, No. 2.

(Continued)

*Primary Examiner*—James Martinell
(74) *Attorney, Agent, or Firm*—Banner & Witcoff, Ltd.

(57) ABSTRACT

This invention provides novel libraries of olfactory receptor odorant/ligand-binding domains and methods of making and using them. The invention also provides libraries of vectors and cells comprising these nucleic acid constructs. The compositions and methods of the invention are used to identify novel ligand-binding domains for olfactory neuron odorant receptors and their ligands. Thus, the compositions and methods of the invention can be used to generate novel odorants, to screen for toxic odorants, or to manipulate an animal's olfactory response.

6 Claims, 1 Drawing Sheet

OTHER PUBLICATIONS

Parmentier, et al., Expression of Members of the Putative Receptor Gene Family . . . , *Nature*, (1992), pp. 453-455, vol. 355, Jan. 30.

Wellerdieck, et al., Functional Expression of Odorant Receptor of the Zebrafish Danio Rerio . . . , *Chemical Senses*, (1997), pp. 467-476, vol. 22.

Afshar, et al., "Towards Structural Models of Molecular Recognition in Olfactory Receptors", *Biochimie*, (1998), pp. 129-135, vol. 80, Feb.

Rouquier, et al., "Distribution of Olfactory Receptor Genes In the Human Genome", *Nature Genetics*, (1998), pp. 243-250, vol. 18.

SEQUENCE LISTING

<160> NUMBER OF SEQ ID NOS: 57

<210> SEQ ID NO 1
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (20)...(23)
<223> OTHER INFORMATION: n=A, G, or a pyrimidine derivative (dP-CE Phosphoramidite)

<400> SEQUENCE: 1
ggggtccgga grsrtadatn anngg                                        25

<210> SEQ ID NO 2
<211> LENGTH: 30
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)...(30)
<223> OTHER INFORMATION: n = A,T,C or G

<400> SEQUENCE: 2
ggggctgcag acaccnatgt ayytnttyyt                                   30

<210> SEQ ID NO 3
<211> LENGTH: 20
<212> TYPE: PRT
<213> ORGANISM: Bovus

-continued

```
<220> FEATURE:
<223> OTHER INFORMATION: PCR primer

<400> SEQUENCE: 3

Met Asn Gly Thr Glu Gly Pro Asn Phe Tyr Val Pro Phe Ser Asn Lys
 1               5                  10                  15

Thr Gly Val Val
            20

<210> SEQ ID NO 4
<211> LENGTH: 174
<212> TYPE: DNA
<213> ORGANISM: Mus musculus
<220> FEATURE:
<223> OTHER INFORMATION: PCR primer

<400> SEQUENCE: 4
gaattccccg gtcagaacta cagcaccata tcagaattta tcctctttgg tttctcagcc      60
ttcccacacc agatgctccc tgctctgttc ctgctctact tgctgatgta tttgttcact     120
cttctgggga acctggtcat catggctgct atctggacag aacatagact gcag           174

<210> SEQ ID NO 5
<211> LENGTH: 87
<212> TYPE: DNA
<213> ORGANISM: Mus musculus
<220> FEATURE:
<223> OTHER INFORMATION: PCR primer

<400> SEQUENCE: 5
tccggaaagg agctgaagaa tgctataatt aaaagcttcc acaggaatgt ctgtcaacaa      60
agtatctaag tgtcagttct gtctaga                                          87

<210> SEQ ID NO 6
<211> LENGTH: 112
<212> TYPE: DNA
<213> ORGANISM: Bovus
<220> FEATURE:
<223> OTHER INFORMATION: PCR primer

<400> SEQUENCE: 6
ggatccgggt tcgcgccgcc ggcgggcagc cgcaagggcc gcagccatga acgggaccga      60
gggcccaaac ttctacgtgc ctttctccaa caagacgggc gtggtggaat tc             112

<210> SEQ ID NO 7
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (20)...(23)
<223> OTHER INFORMATION: n=A, G, or a pyrimidine derivative (dP-CE
      Phosphoramidite)

<400> SEQUENCE: 7
ggggtccgga grstradatn anngg                                            25

<210> SEQ ID NO 8
<211> LENGTH: 30
<212> TYPE: DNA
<213> ORGANISM: Artificial Sequence
<220> FEATURE:
<223> OTHER INFORMATION: PCR primer
```

```
<220> FEATURE:
<221> NAME/KEY: misc_feature
<222> LOCATION: (1)...(30)
<223> OTHER INFORMATION: n = A,T,C or G

<400> SEQUENCE: 8
ggggctgcag acaccnatgt ayytnttyyt                                          30

<210> SEQ ID NO 9
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)...(25)
<223> OTHER INFORMATION: n = A,T,C or G

<400> SEQUENCE: 9
ggggtccgga grstradatn anngg                                               25

<210> SEQ ID NO 10
<211> LENGTH: 30
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)...(30)
<223> OTHER INFORMATION: n = A,T,C or G

<400> SEQUENCE: 10
ggggctgcag acaccnatgt ayytnttyyt                                          30

<210> SEQ ID NO 11
<211> LENGTH: 669
<212> TYPE: DNA
<213> ORGANISM: Mus musculus
<220> FEATURE:
<223> OTHER INFORMATION: PCR primer

<400> SEQUENCE: 11
agtgtcttat ccattctgga tatgggctat gtcaccacca cagtgcccca gatgctggta          60
catctggtct gtaagaagaa gaccatatcc tatgttggat gtgtggctca gatgtacatc        120
ttcctgatgc tgggaatcac cgagtcttgg ctgtttgcaa tcatggccta tgataggtat        180
gtggccattt gccatcccct cagatacaaa gtcatcatga gtcctttgct gcgcgggtca        240
ctggtagcct tctgtgggtt ctggggtatc acctgtgccc tgatatatac tgtttctgct        300
atgattcttc cctactgtgg ccccaatgag atcaaccact tcttctgtga agtgcctgct        360
gtcctgaagc tggcctgcgc agacacctct cccaatgacc aggtagactt catcctaggc        420
tttatccttc ttttggtccc actctccctc atcattgttg tctacatcaa tatctttgct        480
gctatcttga gaatccgttc aactcaaggg aggatcaagg ccttctccac ctgtgtgtcc        540
cacatcactg tggtcaccat gttctccatc ccgtgtatgg ttatgtatat gaggcctggc        600
tctgagtcct ccccagaaga ggacaagaag ttggctctgt tctacaacgt catctctgcc        660
ttcctcaac                                                                669

<210> SEQ ID NO 12
<211> LENGTH: 223
<212> TYPE: PRT
```

<213> ORGANISM: Mus musculus
<220> FEATURE:
<223> OTHER INFORMATION: PCR primer

<400> SEQUENCE: 12

```
Ser Val Leu Ser Ile Leu Asp Met Gly Tyr Val Thr Thr Val Pro
  1               5                  10                  15

Gln Met Leu Val His Leu Val Cys Lys Lys Thr Ile Ser Tyr Val
             20                  25                  30

Gly Cys Val Ala Gln Met Tyr Ile Phe Leu Met Leu Gly Ile Thr Glu
         35                  40                  45

Ser Trp Leu Phe Ala Ile Met Ala Tyr Asp Arg Tyr Val Ala Ile Cys
 50                  55                  60

His Pro Leu Arg Tyr Lys Val Ile Met Ser Pro Leu Leu Arg Gly Ser
 65                  70                  75                  80

Leu Val Ala Phe Cys Gly Phe Trp Gly Ile Thr Cys Ala Leu Ile Tyr
                 85                  90                  95

Thr Val Ser Ala Met Ile Leu Pro Tyr Cys Gly Pro Asn Glu Ile Asn
                100                 105                 110

His Phe Phe Cys Glu Val Pro Ala Val Leu Lys Leu Ala Cys Ala Asp
                115                 120                 125

Thr Ser Pro Asn Asp Gln Val Asp Phe Ile Leu Gly Phe Ile Leu Leu
130                 135                 140

Leu Val Pro Leu Ser Leu Ile Ile Val Val Tyr Ile Asn Ile Phe Ala
145                 150                 155                 160

Ala Ile Leu Arg Ile Arg Ser Thr Gln Gly Arg Ile Lys Ala Phe Ser
                165                 170                 175

Thr Cys Val Ser His Ile Thr Val Thr Met Phe Ser Ile Pro Cys
                180                 185                 190

Met Val Met Tyr Met Arg Pro Gly Ser Glu Ser Pro Glu Glu Asp
                195                 200                 205

Lys Lys Leu Ala Leu Phe Tyr Asn Val Ile Ser Ala Phe Leu Asn
210                 215                 220
```

<210> SEQ ID NO 13
<211> LENGTH: 669
<212> TYPE: DNA
<213> ORGANISM: Mus musculus
<220> FEATURE:
<223> OTHER INFORMATION: PCR primer

<400> SEQUENCE: 13

```
tgcaacctgg ccaccatgga cattgtgtgc accccctctg tgattcctaa ggccctgatt      60
ggcctagtgt ctgaagaaaa caccatctcc ttcaaaggat gcatggctca gctcttcttt     120
cttctgtggt ccttgtcttc ggagctgctg ctgctcacgg tcatggccta tgaccgctat     180
gtggccatct gctttcccct gcactacagc tctagaatga gcccacagct ctgtggggcc     240
ctggccgtgg gtgtatggtc catctgtgct gtgaatgcat ctgtgcacac tggcctgatg     300
acacggctgt cattctgtgg ccccaaggtc atcacccact tcttctgtga gattccccca     360
ctcctcctgc tttcctgtag tcccacatac attaatagcg ttatgacact tgtggcagat     420
gcctttatg ggtgcatcaa ctttgtgcta accttgttat cctatggctg catcattgcc      480
agtgttctgc gcatgcgttc tgctgagggc aagaggaagg ccttttctac ctgttcatcc     540
cacctcatcg tggtctcagt gtactactca tctgtgttct gtgccatgt cagtcctgcc      600
tccagctaca gcccagaaag aagcaaagtt acctccgtgc tgtactcgat cctcagccca     660
``` accctgaac 669

<210> SEQ ID NO 14
<211> LENGTH: 223
<212> TYPE: PRT
<213> ORGANISM: Mus musculus
<220> FEATURE:
<223> OTHER INFORMATION: PCR primer

<400> SEQUENCE: 14

```
Cys Asn Leu Ala Thr Met Asp Ile Val Cys Thr Pro Ser Val Ile Pro
  1               5                  10                  15

Lys Ala Leu Ile Gly Leu Val Ser Glu Glu Asn Thr Ile Ser Phe Lys
             20                  25                  30

Gly Cys Met Ala Gln Leu Phe Phe Leu Leu Trp Ser Leu Ser Ser Glu
         35                  40                  45

Leu Leu Leu Leu Thr Val Met Ala Tyr Asp Arg Tyr Val Ala Ile Cys
     50                  55                  60

Phe Pro Leu His Tyr Ser Ser Arg Met Ser Pro Gln Leu Cys Gly Ala
 65                  70                  75                  80

Leu Ala Val Gly Val Trp Ser Ile Cys Ala Val Asn Ala Ser Val His
                 85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Ser Cys Ser Pro
        115                 120                 125

Thr Tyr Ile Asn Ser Val Met Thr Leu Val Ala Asp Ala Phe Tyr Gly
    130                 135                 140

Cys Ile Asn Phe Val Leu Thr Leu Leu Ser Tyr Gly Cys Ile Ile Ala
145                 150                 155                 160

Ser Val Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Val
            180                 185                 190

Phe Cys Ala Tyr Val Ser Pro Ala Ser Ser Tyr Ser Pro Glu Arg Ser
        195                 200                 205

Lys Val Thr Ser Val Leu Tyr Ser Ile Leu Ser Pro Thr Leu Asn
    210                 215                 220
```

<210> SEQ ID NO 15
<211> LENGTH: 669
<212> TYPE: DNA
<213> ORGANISM: Mus musculus
<220> FEATURE:
<223> OTHER INFORMATION: PCR primer

<400> SEQUENCE: 15

```
tgcaacctgg ccaccatgga tattatctgc acctcctctg tgctgcccaa ggcgctggtt    60
ggtctactat ctgaggaaaa caccatctcc tttaaagggt gcatggccca gctcttcttc   120
cttgtgtggt ccttgtcttc agagctgctg ctgctcacag tcatggccta tgaccgctat   180
gtggccatct gctttcccct gcactacagc tctagaatga gcccacagtt gtgtggggct   240
ctggccatgg gtgtatggtc catctgtgct ctgaatgcat ctatcaacac tggtctgatg   300
acacggctgt cattctgtgg acccaaggtc atcaccccact tcttctgtga gattccccca   360
ctccttctgc tctcctgtag ccccacatac gtaaacagca ttatgactct aatagcagat   420
```

-continued

```
gtcttctatg gaggcatcaa ttttgtgctt accttactat cctatggctg catcattgcc    480
agcatcctgc gcatgcgttc tgctgagggc aagaggaagg ccttttctac ctgctcatcc    540
cacctcatcg tggtctctgt gtactactca tctgtgttct gtgcctatgt cagccctgca    600
tccagctata gcccagaaag aagcaaagtt acctctgtgt tgtactcatt cctcagccca    660
accctgaac                                                             669
```

<210> SEQ ID NO 16
<211> LENGTH: 223
<212> TYPE: PRT
<213> ORGANISM: Mus musculus
<220> FEATURE:
<223> OTHER INFORMATION: PCR primer

<400> SEQUENCE: 16

```
Cys Asn Leu Ala Thr Met Asp Ile Ile Cys Thr Ser Ser Val Leu Pro
  1               5                  10                  15

Lys Ala Leu Val Gly Leu Leu Ser Glu Glu Asn Thr Ile Ser Phe Lys
             20                  25                  30

Gly Cys Met Ala Gln Leu Phe Phe Leu Val Trp Ser Leu Ser Ser Glu
         35                  40                  45

Leu Leu Leu Leu Thr Val Met Ala Tyr Asp Arg Tyr Val Ala Ile Cys
     50                  55                  60

Phe Pro Leu His Tyr Ser Ser Arg Met Ser Pro Gln Leu Cys Gly Ala
 65                  70                  75                  80

Leu Ala Met Gly Val Trp Ser Ile Cys Ala Leu Asn Ala Ser Ile Asn
                 85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Ser Cys Ser Pro
        115                 120                 125

Thr Tyr Val Asn Ser Ile Met Thr Leu Ile Ala Asp Val Phe Tyr Gly
    130                 135                 140

Gly Ile Asn Phe Val Leu Thr Leu Leu Ser Tyr Gly Cys Ile Ile Ala
145                 150                 155                 160

Ser Ile Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Val
            180                 185                 190

Phe Cys Ala Tyr Val Ser Pro Ala Ser Ser Tyr Ser Pro Glu Arg Ser
        195                 200                 205

Lys Val Thr Ser Val Leu Tyr Ser Phe Leu Ser Pro Thr Leu Asn
    210                 215                 220
```

<210> SEQ ID NO 17
<211> LENGTH: 675
<212> TYPE: DNA
<213> ORGANISM: Mus musculus
<220> FEATURE:
<223> OTHER INFORMATION: PCR primer

<400> SEQUENCE: 17

```
gccacccttt cctgtgttga catcctcttc acctccacca cagtgcccaa ggccctagtg     60
aacatccaca cccaaagcag acaatctcc tatgcaggat gcctggtcca gctctatttt    120
ttcctgactt ttggagacat ggacatcttt ctcctggcca caatggccta tgaccgcttt    180
gtagctattt gtcaccctct ccactatagg atgatcatga gcttccagcg ctgctcactc    240
```

```
ttagtgacag tctgttggac ccttacaacc gttgtggcca tgacacacac cttcctcata      300
ttccggctct ccttctgctc tcagaaggtc attccagact tcttctgtga cctgggaccc      360
ctaatgaaga tcgcttgctc tgaaacccgg atcaatgagc ttgtgcttct cttcctgggg      420
ggtgcagtca tcttaatccc cttttttgctc atccttatgt cttatatccg cattgtttca     480
gccatcctca gggtcccttc tgcccaagga aggcgtaagg ccttttctac ctgtgggtcc      540
cacctttctg tggtggccct attctttggg actgtgataa gggcttatct atgtccttca      600
tcctcttcct ctaactcagt ggtagaggac acagcagcag ctgtcatgta tacagtggtg      660
actcccgtgc tgaac                                                      675
```

<210> SEQ ID NO 18
<211> LENGTH: 225
<212> TYPE: PRT
<213> ORGANISM: Mus musculus
<220> FEATURE:
<223> OTHER INFORMATION: PCR primer

<400> SEQUENCE: 18

```
Ala Thr Leu Ser Cys Val Asp Ile Leu Phe Thr Ser Thr Thr Val Pro
 1               5                  10                  15

Lys Ala Leu Val Asn Ile His Thr Gln Ser Arg Thr Ile Ser Tyr Ala
            20                  25                  30

Gly Cys Leu Val Gln Leu Tyr Phe Phe Leu Thr Phe Gly Asp Met Asp
        35                  40                  45

Ile Phe Leu Leu Ala Thr Met Ala Tyr Asp Arg Phe Val Ala Ile Cys
    50                  55                  60

His Pro Leu His Tyr Arg Met Ile Met Ser Phe Gln Arg Cys Ser Leu
65                  70                  75                  80

Leu Val Thr Val Cys Trp Thr Leu Thr Thr Val Ala Met Thr His
                85                  90                  95

Thr Phe Leu Ile Phe Arg Leu Ser Phe Cys Ser Gln Lys Val Ile Pro
            100                 105                 110

Asp Phe Phe Cys Asp Leu Gly Pro Leu Met Lys Ile Ala Cys Ser Glu
        115                 120                 125

Thr Arg Ile Asn Glu Leu Val Leu Leu Phe Leu Gly Gly Ala Val Ile
    130                 135                 140

Leu Ile Pro Phe Leu Leu Ile Leu Met Ser Tyr Ile Arg Ile Val Ser
145                 150                 155                 160

Ala Ile Leu Arg Val Pro Ser Ala Gln Gly Arg Lys Ala Phe Ser
                165                 170                 175

Thr Cys Gly Ser His Leu Ser Val Val Ala Leu Phe Phe Gly Thr Val
            180                 185                 190

Ile Arg Ala Tyr Leu Cys Pro Ser Ser Ser Ser Asn Ser Val Val
        195                 200                 205

Glu Asp Thr Ala Ala Ala Val Met Tyr Thr Val Val Thr Pro Val Leu
    210                 215                 220

Asn
225
```

<210> SEQ ID NO 19
<211> LENGTH: 669
<212> TYPE: DNA
<213> ORGANISM: Mus musculus
<220> FEATURE:
<223> OTHER INFORMATION: PCR primer

<400> SEQUENCE: 19

```
agtcagctct ccctcatgga cctcatgctg gtctgtaaca ttgtgccaaa gatggcagtc    60
aacttcctgt ctggcaggaa gtccatctct tttgccggct gtggcataca aatcggattt   120
tttgtctctc ttgtgggatc agagggtctc ttgttaggac tcatggctta tgatcgctat   180
gtggccatta gccacccact tcactatccc attctcatga ccaaaaggt ctgtctccag    240
attgctggaa gttcctgggc ttttgggatc cttgatggaa taattcagat ggtggcagcc   300
atgagcctgc cctactgtgg ctcacggtat atagatcact tcttctgtga agtgccggct   360
ttactgaagc tggcctgtgc agacacctcc cttttcgaca ccctgctctt tgcttgctgt   420
gtctttatgc tgcttcttcc tttctcgatc attgtgactt cctatgctcg catcttgggg   480
gctgtgctcc gtatgcactc tgcccagtcc cgaaaaaagg ccctggccac ttgttcctcc   540
cacctgacag ctgtctctct cttctacggg gcagcaatgt tcatctacct gaggccaagg   600
cgatatcgcg ctcctagcca tgacaaagtt gtctcaatct tctacacagt tcttactcct   660
atgctcaac                                                          669
```

<210> SEQ ID NO 20
<211> LENGTH: 223
<212> TYPE: PRT
<213> ORGANISM: Mus musculus
<220> FEATURE:
<223> OTHER INFORMATION: PCR primer

<400> SEQUENCE: 20

```
Ser Gln Leu Ser Leu Met Asp Leu Met Leu Val Cys Asn Ile Val Pro
  1               5                  10                  15
Lys Met Ala Val Asn Phe Leu Ser Gly Arg Lys Ser Ile Ser Phe Ala
             20                  25                  30
Gly Cys Gly Ile Gln Ile Gly Phe Phe Val Ser Leu Val Gly Ser Glu
         35                  40                  45
Gly Leu Leu Leu Gly Leu Met Ala Tyr Asp Arg Tyr Val Ala Ile Ser
     50                  55                  60
His Pro Leu His Tyr Pro Ile Leu Met Ser Gln Lys Val Cys Leu Gln
 65                  70                  75                  80
Ile Ala Gly Ser Ser Trp Ala Phe Gly Ile Leu Asp Gly Ile Ile Gln
                 85                  90                  95
Met Val Ala Ala Met Ser Leu Pro Tyr Cys Gly Ser Arg Tyr Ile Asp
            100                 105                 110
His Phe Phe Cys Glu Val Pro Ala Leu Leu Lys Leu Ala Cys Ala Asp
        115                 120                 125
Thr Ser Leu Phe Asp Thr Leu Leu Phe Ala Cys Cys Val Phe Met Leu
    130                 135                 140
Leu Leu Pro Phe Ser Ile Ile Val Thr Ser Tyr Ala Arg Ile Leu Gly
145                 150                 155                 160
Ala Val Leu Arg Met His Ser Ala Gln Ser Arg Lys Lys Ala Leu Ala
                165                 170                 175
Thr Cys Ser Ser His Leu Thr Ala Val Ser Leu Phe Tyr Gly Ala Ala
            180                 185                 190
Met Phe Ile Tyr Leu Arg Pro Arg Tyr Arg Ala Pro Ser His Asp
        195                 200                 205
Lys Val Val Ser Ile Phe Tyr Thr Val Leu Thr Pro Met Leu Asn
    210                 215                 220
```

```
<210> SEQ ID NO 21
<211> LENGTH: 669
<212> TYPE: DNA
<213> ORGANISM: Mus musculus
<220> FEATURE:
<223> OTHER INFORMATION: PCR primer

<400> SEQUENCE: 21
tacaaccttt cattgtctga catgggcttt agcagcacca caatccccaa aatgctgata      60
aacttgcatg cacataagag atccacaaca tatgctgaat gcctaactca ggtatctttc    120
tttattcttt ttgggtgtat ggacagcttt ctactggcag tgatggcata tgaccgatgg    180
gtggccattt gtcaccctct acactaccaa gtcattctga atccttgtcg gtgtagatat    240
ttggttgtaa tgtcattttg tatcagtctc attgattcac aggtgcactg ctttatggtg    300
tcacaactaa catttttgtac taatatagaa atccctcatt tcttctgtga tgttccagaa    360
cttgtaaaac ttgcttgttc taacactact atcaatgaca tagccatgtt tctttcaagc    420
atcattgttg gattcctccc tgcctcagga atattttact cctactataa aattacttct    480 tctatttta gagttccatc actgttaggg aaatataaag ccttctctac ctgtggatct    540
cacctgtcag ttgtttgcct attttatgga acaggtatag gagtttacct cagttccaca    600
gtttctggtt cttccaggga aagtatggta gcttcggtaa tgtatacaat ggtggttcct    660
atgatgaac                                                           669

<210> SEQ ID NO 22
<211> LENGTH: 223
<212> TYPE: PRT
<213> ORGANISM: Mus musculus
<220> FEATURE:
<223> OTHER INFORMATION: PCR primer

<400> SEQUENCE: 22

Tyr Asn Leu Ser Leu Ser Asp Met Gly Phe Ser Thr Thr Ile Pro
 1               5                  10                  15

Lys Met Leu Ile Asn Leu His Ala His Lys Arg Ser Thr Thr Tyr Ala
             20                  25                  30

Glu Cys Leu Thr Gln Val Ser Phe Phe Ile Leu Phe Gly Cys Met Asp
         35                  40                  45

Ser Phe Leu Leu Ala Val Met Ala Tyr Asp Arg Trp Val Ala Ile Cys
     50                  55                  60

His Pro Leu His Tyr Gln Val Ile Leu Asn Pro Cys Arg Cys Arg Tyr
 65                  70                  75                  80

Leu Val Val Met Ser Phe Cys Ile Ser Leu Ile Asp Ser Gln Val His
                 85                  90                  95

Cys Phe Met Val Ser Gln Leu Thr Phe Cys Thr Asn Ile Glu Ile Pro
            100                 105                 110

His Phe Cys Asp Val Pro Glu Leu Val Lys Leu Ala Cys Ser Asn
        115                 120                 125

Thr Thr Ile Asn Asp Ile Ala Met Phe Leu Ser Ser Ile Ile Val Gly
    130                 135                 140

Phe Leu Pro Ala Ser Gly Ile Phe Tyr Ser Tyr Lys Ile Thr Ser
145                 150                 155                 160

Ser Ile Phe Arg Val Pro Ser Leu Leu Gly Lys Tyr Lys Ala Phe Ser
                165                 170                 175

Thr Cys Gly Ser His Leu Ser Val Val Cys Leu Phe Tyr Gly Thr Gly
            180                 185                 190
```

-continued

```
Ile Gly Val Tyr Leu Ser Ser Thr Val Ser Gly Ser Ser Arg Glu Ser
        195                 200                 205
Met Val Ala Ser Val Met Tyr Thr Met Val Val Pro Met Met Asn
    210                 215                 220

<210> SEQ ID NO 23
<211> LENGTH: 669
<212> TYPE: DNA
<213> ORGANISM: Mus musculus
<220> FEATURE:
<223> OTHER INFORMATION: PCR primer

<400> SEQUENCE: 23
agtcagctct ccctcatgga cctcatgctg gtctgtaaca ttgtgccaaa gatggcagtc      60
aacttcctgt ctggcaggaa gtccatctct tttgccggct gtggcataca aatcggattt    120
tttgtctctc ttgtgggatc agagggtctc ttgttaggac tcatggctta tgatcgctat    180
gtggccatta gccacccact tcactatccc attctcatga gccaaaaggt ctgtctccag    240
attgctggaa gttcctgggc ttttgggatc cttgatggaa taattcagat ggtggcagcc    300
atgagcctgc cctactgtgg ctcacggtat atagatcact tcttctgtga agtgccggct    360
ttactgaagc tggcctgtgc agacacctcc cttttcgaca ccctgctctt tgcttgctgt    420
gtctttatgc tgcttcttcc tttctcgatc attgtgactt cctatgctcg catcttgggg    480
actgtgctcc gtatgcactc tgcccagtcc cgaaaaaagg ccctggccac ttgttcctcc    540
cacctgacag ctgtctctct cttctacggg gcagcaatgt tcatctacct gaggccaagg    600
cgatatcgcg ctcctagcca tgacaaagtt gtctcaatct tctacacagt tcttactcct    660
atgctcaac                                                             669

<210> SEQ ID NO 24
<211> LENGTH: 223
<212> TYPE: PRT
<213> ORGANISM: Mus musculus
<220> FEATURE:
<223> OTHER INFORMATION: PCR primer

<400> SEQUENCE: 24

Ser Gln Leu Ser Leu Met Asp Leu Met Leu Val Cys Asn Ile Val Pro
1               5                   10                  15
Lys Met Ala Val Asn Phe Leu Ser Gly Arg Lys Ser Ile Ser Phe Ala
            20                  25                  30
Gly Cys Gly Ile Gln Ile Gly Phe Phe Val Ser Leu Val Gly Ser Glu
        35                  40                  45
Gly Leu Leu Leu Gly Leu Met Ala Tyr Asp Arg Tyr Val Ala Ile Ser
    50                  55                  60
His Pro Leu His Tyr Pro Ile Leu Met Ser Gln Lys Val Cys Leu Gln
65                  70                  75                  80
Ile Ala Gly Ser Ser Trp Ala Phe Gly Ile Leu Asp Gly Ile Ile Gln
                85                  90                  95
Met Val Ala Ala Met Ser Leu Pro Tyr Cys Gly Ser Arg Tyr Ile Asp
            100                 105                 110
His Phe Phe Cys Glu Val Pro Ala Leu Leu Lys Leu Ala Cys Ala Asp
        115                 120                 125
Thr Ser Leu Phe Asp Thr Leu Leu Phe Ala Cys Cys Val Phe Met Leu
    130                 135                 140
Leu Leu Pro Phe Ser Ile Ile Val Thr Ser Tyr Ala Arg Ile Leu Gly
```

```
                145                 150                 155                 160
Thr Val Leu Arg Met His Ser Ala Gln Ser Arg Lys Lys Ala Leu Ala
                165                 170                 175

Thr Cys Ser Ser His Leu Thr Ala Val Ser Leu Phe Tyr Gly Ala Ala
            180                 185                 190

Met Phe Ile Tyr Leu Arg Pro Arg Arg Tyr Arg Ala Pro Ser His Asp
        195                 200                 205

Lys Val Val Ser Ile Phe Tyr Thr Val Leu Thr Pro Met Leu Asn
    210                 215                 220
```

<210> SEQ ID NO 25
<211> LENGTH: 669
<212> TYPE: DNA
<213> ORGANISM: Mus musculus
<220> FEATURE:
<223> OTHER INFORMATION: PCR primer

<400> SEQUENCE: 25

```
tctaatctgt cctttgtgga catctgcttc acttccacca ctgttccaca gatgctggta      60
aacattcaca cacaaagcaa ggccatcacc tatgcaggct gcatcatcca aatgtacttc     120
ttactgcttt tttcagggtt agacatcttt ctgctgactg tgatggccta tgaccgctat     180
gtggccatct gtcaccccct gcattacatg atcatcatga gcacaagacg ctgtggattg     240
atgattctgg catgctggat tataggtgtt ataaattccc tgttacacac cttttttggtg    300
ttacggctgt cattctgcac aaacttggaa atcccccatt ttttctgtga acttaatcaa     360
gttgtacacc aggcctgttc tgacaccttt cttaatgata tggtaattta cattacagct     420
atgctactgg ctgttggccc cttctctggt atcctttact cttactctag gatagtatcc     480
tccatttgtg caatctcctc agtgcagggg aagtacaaag cattttccac ctgtgcatct     540
cacctctcag ttgtctcctt attttattgc accctcctgg gagtgtacct cagctctgct     600
gtgacccaaa actcacatgc tactgcaaca gcttcattga tgtacactgt ggtcaccccc     660
atgctgaac                                                             669
```

<210> SEQ ID NO 26
<211> LENGTH: 223
<212> TYPE: PRT
<213> ORGANISM: Mus musculus
<220> FEATURE:
<223> OTHER INFORMATION: PCR primer

<400> SEQUENCE: 26

```
Ser Asn Leu Ser Phe Val Asp Ile Cys Phe Thr Ser Thr Val Pro
1               5                   10                  15
Gln Met Leu Val Asn Ile His Thr Gln Ser Lys Ala Ile Thr Tyr Ala
                20                  25                  30
Gly Cys Ile Ile Gln Met Tyr Phe Leu Leu Phe Ser Gly Leu Asp
            35                  40                  45
Ile Phe Leu Leu Thr Val Met Ala Tyr Asp Arg Tyr Val Ala Ile Cys
    50                  55                  60
His Pro Leu His Tyr Met Ile Ile Met Ser Thr Arg Arg Cys Gly Leu
65                  70                  75                  80
Met Ile Leu Ala Cys Trp Ile Ile Gly Val Ile Asn Ser Leu Leu His
                85                  90                  95
Thr Phe Leu Val Leu Arg Leu Ser Phe Cys Thr Asn Leu Glu Ile Pro
                100                 105                 110
```

```
His Phe Phe Cys Glu Leu Asn Gln Val Val His Gln Ala Cys Ser Asp
            115                 120                 125

Thr Phe Leu Asn Asp Met Val Ile Tyr Ile Thr Ala Met Leu Leu Ala
    130                 135                 140

Val Gly Pro Phe Ser Gly Ile Leu Tyr Ser Tyr Ser Arg Ile Val Ser
145                 150                 155                 160

Ser Ile Cys Ala Ile Ser Ser Val Gln Gly Lys Tyr Lys Ala Phe Ser
                165                 170                 175

Thr Cys Ala Ser His Leu Ser Val Val Ser Leu Phe Tyr Cys Thr Leu
            180                 185                 190

Leu Gly Val Tyr Leu Ser Ser Ala Val Thr Gln Asn Ser His Ala Thr
        195                 200                 205

Ala Thr Ala Ser Leu Met Tyr Thr Val Thr Pro Met Leu Asn
    210                 215                 220
```

<210> SEQ ID NO 27
<211> LENGTH: 669
<212> TYPE: DNA
<213> ORGANISM: Mus musculus
<220> FEATURE:
<223> OTHER INFORMATION: PCR primer

<400> SEQUENCE: 27

```
agtcagctct ccctcatgga cctcatgctg gtctgtaaca ttgtgccaaa gatggcagtc      60
aacttcctgt ctggcaggaa gtccatctct tttgccggct gtggcataca aatcggattt     120
tttgtctctc ttgtgggatc agagggtctc ttgttaggac tcatggctta tgatcgctat     180
gtggccatta gccacccact tcactatccc attctcatga gccaaaaggt ctgtctccag     240
attgctggaa gttcctgggc ttttgggatc cttgatggaa taattcagat ggtggcagcc     300
atgagcctgc cctactgtgg ctcacggtat atagatcact tcttctgtga agtgccggct     360
ttactgaagc tggcctgtgc agacacctcc cttttcgaca ccctgctctt tgcttgctgt     420
gtctttatgc tgcttcttcc tttctcgatc attgtgactt cctatgctcg catcttgggg     480
gctgtgctcc gtatgcactc tgcccagtcc cgaaaaaagg ccctggccac ttgttcctcc     540
cacctgacag ctgtctctct cttctacggg gcagcaatgt tcatctacct gaggccaagg     600
cgatatcgcg ctcctagcca tgacaaagtt gtctcaatct tctacacagt tcttactcct     660
atgctcaac                                                              669
```

<210> SEQ ID NO 28
<211> LENGTH: 223
<212> TYPE: PRT
<213> ORGANISM: Mus musculus
<220> FEATURE:
<223> OTHER INFORMATION: PCR primer

<400> SEQUENCE: 28

```
Ser Gln Leu Ser Leu Met Asp Leu Met Leu Val Cys Asn Ile Val Pro
1               5                  10                  15

Lys Met Ala Val Asn Phe Leu Ser Gly Arg Lys Ser Ile Ser Phe Ala
            20                  25                  30

Gly Cys Gly Ile Gln Ile Gly Phe Phe Val Ser Leu Val Gly Ser Glu
        35                  40                  45

Gly Leu Leu Leu Gly Leu Met Ala Tyr Asp Arg Tyr Val Ala Ile Ser
    50                  55                  60

His Pro Leu His Tyr Pro Ile Leu Met Ser Gln Lys Val Cys Leu Gln
65                  70                  75                  80
```

```
Ile Ala Gly Ser Ser Trp Ala Phe Gly Ile Leu Asp Gly Ile Gln
                85                  90                  95

Met Val Ala Ala Met Ser Leu Pro Tyr Cys Gly Ser Arg Tyr Ile Asp
            100                 105                 110

His Phe Cys Glu Val Pro Ala Leu Leu Lys Leu Ala Cys Ala Asp
        115                 120                 125

Thr Ser Leu Phe Asp Thr Leu Leu Phe Ala Cys Cys Val Phe Met Leu
    130                 135                 140

Leu Leu Pro Phe Ser Ile Ile Val Thr Ser Tyr Ala Arg Ile Leu Gly
145                 150                 155                 160

Ala Val Leu Arg Met His Ser Ala Gln Ser Arg Lys Lys Ala Leu Ala
                165                 170                 175

Thr Cys Ser Ser His Leu Thr Ala Val Ser Leu Phe Tyr Gly Ala Ala
            180                 185                 190

Met Phe Ile Tyr Leu Arg Pro Arg Arg Tyr Arg Ala Pro Ser His Asp
        195                 200                 205

Lys Val Val Ser Ile Phe Tyr Thr Val Leu Thr Pro Met Leu Asn
210                 215                 220
```

<210> SEQ ID NO 29
<211> LENGTH: 681
<212> TYPE: DNA
<213> ORGANISM: Mus musculus
<220> FEATURE:
<223> OTHER INFORMATION: PCR primer

<400> SEQUENCE: 29

```
tgtgccctct ccatctctga gattttctac acctttgcca tcatcccacg catgttggct      60
gacctgctca ccacacttca ctccatcgcc tttctggcct gtgccagcca gatgttcttc     120
tccttcacat ttggcttcac ccattccttt ctactcaccg tcatgggcta tgaccgctac     180
gtggccatct gtcacccact gagatacaat gtgctcatga gccccgtgg ctgtgcctgc     240
ctggtagcct ggtcctgggt tggtggatca ttcatgggga cagtggtgac gacagccatt     300
ttcaacctca cattctgtgg acccaatgag atccaccatt ttacttgtca tgttccacct     360
ctattgaagt tggcatgcgg agagaatgta ctggaggtgg caaagggtgt agaaatagtg     420
tgcatcacag ccctcctggg ctgctttctc ctcatcctcc tctcatatgc cttcattgtg     480
gttaccatct tgaagatacc atcagctgag ggtcggcaca aggctttctc cacatgtgca     540
tcccacctca cagtggtggt tgtacattat ggctttgctt ctgtcattta cctcaagcct     600
aagggcccca gtctctggaa aggagatact ctgatgggca tcacctacac agtcctcacc     660
cccttcctta gtatgctcaa c                                               681
```

<210> SEQ ID NO 30
<211> LENGTH: 224
<212> TYPE: PRT
<213> ORGANISM: Mus musculus
<220> FEATURE:
<223> OTHER INFORMATION: PCR primer

<400> SEQUENCE: 30

```
Cys Ala Leu Ser Ile Ser Glu Ile Phe Tyr Thr Phe Ala Ile Ile Pro
1               5                   10                  15

Arg Met Leu Ala Asp Leu Leu Thr Thr Leu His Ser Ile Ala Phe Leu
            20                  25                  30

Ala Cys Ala Ser Gln Met Phe Phe Ser Phe Thr Phe Gly Phe Thr His
```

```
                35                  40                  45
Ser Phe Leu Leu Thr Val Met Gly Tyr Asp Arg Tyr Val Ala Ile Cys
    50                  55                  60

His Pro Leu Arg Tyr Asn Val Leu Met Ser Pro Arg Gly Cys Ala Cys
65                  70                  75                  80

Leu Val Ala Trp Ser Trp Val Gly Gly Ser Phe Met Gly Thr Val Val
                85                  90                  95

Thr Thr Ala Ile Phe Asn Leu Thr Phe Cys Gly Pro Asn Glu Ile His
            100                 105                 110

His Phe Thr Cys His Val Pro Pro Leu Leu Lys Leu Ala Cys Gly Glu
        115                 120                 125

Asn Val Leu Glu Val Ala Lys Gly Val Glu Ile Val Cys Ile Thr Ala
    130                 135                 140

Leu Leu Gly Cys Phe Leu Ile Leu Leu Ser Tyr Ala Phe Ile Val
145                 150                 155                 160

Val Thr Ile Leu Lys Ile Pro Ser Ala Glu Gly Arg His Lys Ala Phe
                165                 170                 175

Ser Thr Cys Ala Ser His Leu Thr Val Val Val His Tyr Gly Phe
            180                 185                 190

Ala Ser Val Ile Tyr Leu Lys Pro Lys Gly Pro Lys Ser Leu Glu Gly
        195                 200                 205

Asp Thr Leu Met Gly Ile Thr Tyr Thr Val Leu Thr Pro Phe Leu Ser
    210                 215                 220

<210> SEQ ID NO 31
<211> LENGTH: 669
<212> TYPE: DNA
<213> ORGANISM: Mus musculus
<220> FEATURE:
<223> OTHER INFORMATION: PCR primer

<400> SEQUENCE: 31
tgcaacttag cgaccatgga tattatctgc acctcctctg tactgcccaa ggcgctggtt    60
ggtctactgt ctgaggaaaa caccacctcc ttcaaagggt gcatgactca gctcttcttt   120
cttgtgtggt ctggatcctc tgagctgctg ctgctcacag tcatggccta tgaccgctat   180
gtggccatct gtttgcccct gcattacagc tctaggatga gtccacagct ctgtgggacc   240
tttgccgtgg gtgtatggtc catctgcgca ctaaatgcat ctatcaacac tggtctgatg   300
acacggctgt cattctgtgg ccccaaggtc atcacccact tcttctgtga gattccccca   360
ctcctcctgc tctcctgtag tcctacatat ataaatagcg ttatgactct tgtggcagat   420
gccttttatg gaggcatcaa tttttttactt accttgctat cctatggctg catcattgcc   480
agcatcctgc gcatgcgttc tgctgagggc aagaggaagg ccttttctac ctgctcatcc   540
cacctcattg tggtctctgt gtactactca tctgtgttct gtgccatgt cagccctgct   600 tctagctaca gcccagaaag aagcaaagtt tcctcagtgc tgtactcagt cctcagccca   660
accctcaac                                                            669

<210> SEQ ID NO 32
<211> LENGTH: 223
<212> TYPE: PRT
<213> ORGANISM: Mus musculus
<220> FEATURE:
<223> OTHER INFORMATION: PCR primer

<400> SEQUENCE: 32
```

```
Cys Asn Leu Ala Thr Met Asp Ile Ile Cys Thr Ser Ser Val Leu Pro
  1               5                  10                  15

Lys Ala Leu Val Gly Leu Leu Ser Glu Glu Asn Thr Thr Ser Phe Lys
                 20                  25                  30

Gly Cys Met Thr Gln Leu Phe Phe Leu Val Trp Ser Gly Ser Ser Glu
             35                  40                  45

Leu Leu Leu Leu Thr Val Met Ala Tyr Asp Arg Tyr Val Ala Ile Cys
 50                  55                  60

Leu Pro Leu His Tyr Ser Ser Arg Met Ser Pro Gln Leu Cys Gly Thr
 65                  70                  75                  80

Phe Ala Val Gly Val Trp Ser Ile Cys Ala Leu Asn Ala Ser Ile Asn
                 85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Ser Cys Ser Pro
            115                 120                 125

Thr Tyr Ile Asn Ser Val Met Thr Leu Val Ala Asp Ala Phe Tyr Gly
130                 135                 140

Gly Ile Asn Phe Leu Leu Thr Leu Leu Ser Tyr Gly Cys Ile Ile Ala
145                 150                 155                 160

Ser Ile Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Val
            180                 185                 190

Phe Cys Ala Tyr Val Ser Pro Ala Ser Ser Tyr Ser Pro Glu Arg Ser
            195                 200                 205

Lys Val Ser Ser Val Leu Tyr Ser Val Leu Ser Pro Thr Leu Asn
210                 215                 220

<210> SEQ ID NO 33
<211> LENGTH: 666
<212> TYPE: DNA
<213> ORGANISM: Artificial Sequence
<220> FEATURE:
<223> OTHER INFORMATION: PCR primer

<400> SEQUENCE: 33
gccaaccttt ccttcgttga tgtctgcttc accaccaatc tcatcccag  gctcctggct    60
ggccatgtgg ctggaacaag gaccatctct tatgtccact gcctaactca gacgtacttc   120
ctgatttctt ttgccaatgt ggacaccttt ctgctggctg ccatggccct ggacagattt   180
gtggccatat gctacccact acagtaccac accatcatca ccccccagct ctgtgtgggg   240
ctggcagccg ttgtgtggat gtgctctgcc ctcatctctc tgatgcacac actcctcatg   300
agcagactga gtttctgctc ctccatcccg gagatctctc acttctactg tgatgcttac   360
ctgctcatga agttggcctg ttcagacaca cgagtcaatc aacttgtctt cctgggagct   420
gtggtcctct tgtggccccc tgcattctc  attgtggtct cttatgtccg aatcaccatg   480
gtggtcctcc agatccctc  tgcaaagggc cggcacaaga catttccac  atgtagctca   540
cacttgtctg tggtcactct gttctatggc acagtactgg gtatctatat acgacctcca   600
gactccttct ccacccagga cacggtagcc accatcatgt atactgtggt tacccccatg   660
ctgaac                                                               666

<210> SEQ ID NO 34
<211> LENGTH: 222
```

```
<212> TYPE: PRT
<213> ORGANISM: Mus musculus
<220> FEATURE:
<223> OTHER INFORMATION: PCR primer

<400> SEQUENCE: 34

Ala Asn Leu Ser Phe Val Asp Val Cys Phe Thr Thr Asn Leu Ile Pro
 1               5                  10                  15

Arg Leu Leu Ala Gly His Val Ala Gly Thr Arg Thr Ile Ser Tyr Val
            20                  25                  30

His Cys Leu Thr Gln Thr Tyr Phe Leu Ile Ser Phe Ala Asn Val Asp
        35                  40                  45

Thr Phe Leu Leu Ala Ala Met Ala Leu Asp Arg Phe Val Ala Ile Cys
    50                  55                  60

Tyr Pro Leu Gln Tyr His Thr Ile Ile Thr Pro Gln Leu Cys Val Gly
65                  70                  75                  80

Leu Ala Ala Val Val Trp Met Cys Ser Ala Leu Ile Ser Leu Met His
                85                  90                  95

Thr Leu Leu Met Ser Arg Leu Ser Phe Cys Ser Ser Ile Pro Glu Ile
            100                 105                 110

Ser His Phe Tyr Cys Asp Ala Tyr Leu Leu Met Lys Leu Ala Cys Ser
        115                 120                 125

Asp Thr Arg Val Asn Gln Leu Val Phe Leu Gly Ala Val Val Leu Phe
    130                 135                 140

Val Ala Pro Cys Ile Leu Ile Val Val Ser Tyr Val Arg Ile Thr Met
145                 150                 155                 160

Val Val Leu Gln Ile Pro Ser Ala Lys Gly Arg His Lys Thr Phe Ser
                165                 170                 175

Thr Cys Ser Ser His Leu Ser Val Val Thr Leu Phe Tyr Gly Thr Val
            180                 185                 190

Leu Gly Ile Tyr Ile Arg Pro Pro Asp Ser Phe Ser Thr Gln Asp Thr
        195                 200                 205

Val Ala Thr Ile Met Tyr Thr Val Val Thr Pro Met Leu Asn
    210                 215                 220

<210> SEQ ID NO 35
<211> LENGTH: 669
<212> TYPE: DNA
<213> ORGANISM: Mus musculus
<220> FEATURE:
<223> OTHER INFORMATION: PCR primer

<400> SEQUENCE: 35
tgcaacctgg ctaccacgga tattgtgtgc acctcctctg tgattcctaa ggccctgatt     60
ggcctagtat ctgaggaaaa catcatcacc ttcaagggat gtatgcccca gctcttcttc    120
cttgcatggg caacatccgc agagctgttg ctgctcacgg tcatggccta tgaccgctat    180
gtggctatct gctttcccct acactacagc tctaggatga gcccacagct ctgtggagca    240
ctggccgtgg gtgtatggtc catcagtgct gtgaatgcat ctgtgcacac tggcctgatg    300
acacggctgt cattctgtgg acccaaggtc atcacccact tcttctgtga tacccccca    360 ctcctcctgc tctcctgtag ttccacatac attaatagtg ttatgacact tgtggcagat    420
gtctttctgg gaggcatcaa cttcatgtta accctgttat cttatggctt catcattgcc    480
agcatcctgc gcatgcgttc tgctgagggc aagaggaagg cctttttctac ctgctcatcc    540 cacctcatcg tggtttctgt gtactactca tctctgttct gtgcctatat cagccctgct    600
```

-continued

```
tctagctaca gcccagaaag aagcaaagtt tcctcagtgc tgtactcagt cctcagccca    660
accctcaac                                                            669
```

<210> SEQ ID NO 36
<211> LENGTH: 223
<212> TYPE: PRT
<213> ORGANISM: Mus musculus
<220> FEATURE:
<223> OTHER INFORMATION: PCR primer

<400> SEQUENCE: 36

```
Cys Asn Leu Ala Thr Thr Asp Ile Val Cys Thr Ser Ser Val Ile Pro
  1               5                  10                  15

Lys Ala Leu Ile Gly Leu Val Ser Glu Glu Asn Ile Ile Thr Phe Lys
             20                  25                  30

Gly Cys Met Ala Gln Leu Phe Phe Leu Ala Trp Ala Thr Ser Ala Glu
         35                  40                  45

Leu Leu Leu Thr Val Met Ala Tyr Asp Arg Tyr Val Ala Ile Cys
 50                  55                  60

Phe Pro Leu His Tyr Ser Ser Arg Met Ser Pro Gln Leu Cys Gly Ala
 65                  70                  75                  80

Leu Ala Val Gly Val Trp Ser Ile Ser Ala Val Asn Ala Ser Val His
                 85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Ser Cys Ser Ser
        115                 120                 125

Thr Tyr Ile Asn Ser Val Met Thr Leu Val Ala Asp Val Phe Leu Gly
130                 135                 140

Gly Ile Asn Phe Met Leu Thr Leu Leu Ser Tyr Gly Phe Ile Ile Ala
145                 150                 155                 160

Ser Ile Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Leu
            180                 185                 190

Phe Cys Ala Tyr Ile Ser Pro Ala Ser Ser Tyr Ser Pro Glu Arg Ser
        195                 200                 205

Lys Val Ser Ser Val Leu Tyr Ser Val Leu Ser Pro Thr Leu Asn
    210                 215                 220
```

<210> SEQ ID NO 37
<211> LENGTH: 669
<212> TYPE: DNA
<213> ORGANISM: Mus musculus
<220> FEATURE:
<223> OTHER INFORMATION: PCR primer

<400> SEQUENCE: 37

```
agcaacctgg cttttgttga tttctgctac tcctctgtca ttacacctaa gatgcttggg     60
aatttcttgt atagcaaaaa tgccatatcc ttcaatgcat gtgctgccca gttaggctgc    120
tttctcacat ttatggtatc agagtgcttg ctcctggctt ccatggcata tgatagatat    180
gcagcaattt gtaaccctct attgtatatg gtcacaatgt ctcctggaat ctgcattcag    240
cttgtagttg tgccctatag ctatagtttc tcatggcat tgattcacac tcttctaacc    300
ttccgcctat cctattgcca ttctaatatc atcaatcact tctactgtga tgacatgcct    360
cttctcaggc taacttgctc agatactcac tacaagcagc tgtctatttt ggcctgtgct    420
```

```
ggaatcacat tcatttcttc tgttctgatt gtttctgtat cctacatgtt cattatttct    480
gccattctga ggatgcgctc agctgaagga agacggaaag ccttttccac ctgtagctct    540
cacatgatgg cagtgagcat attctatgga actcttatct ttatgtactt acagccgagc    600
tctgaccatt ctcttgatac agataagatg gcctctgtct tctacacagt gatcatcccc    660
atgttgaac                                                             669
```

<210> SEQ ID NO 38
<211> LENGTH: 223
<212> TYPE: PRT
<213> ORGANISM: Mus musculus
<220> FEATURE:
<223> OTHER INFORMATION: PCR primer

<400> SEQUENCE: 38

```
Ser Asn Leu Ala Phe Val Asp Phe Cys Tyr Ser Ser Val Ile Thr Pro
 1               5                  10                  15

Lys Met Leu Gly Asn Phe Leu Tyr Ser Lys Asn Ala Ile Ser Phe Asn
            20                  25                  30

Ala Cys Ala Ala Gln Leu Gly Cys Phe Leu Thr Phe Met Val Ser Glu
        35                  40                  45

Cys Leu Leu Leu Ala Ser Met Ala Tyr Asp Arg Tyr Ala Ala Ile Cys
    50                  55                  60

Asn Pro Leu Leu Tyr Met Val Thr Met Ser Pro Gly Ile Cys Ile Gln
65                  70                  75                  80

Leu Val Val Val Pro Tyr Ser Tyr Ser Phe Leu Met Ala Leu Ile His
                85                  90                  95

Thr Leu Leu Thr Phe Arg Leu Ser Tyr Cys His Ser Asn Ile Ile Asn
            100                 105                 110

His Phe Tyr Cys Asp Asp Met Pro Leu Leu Arg Leu Thr Cys Ser Asp
        115                 120                 125

Thr His Tyr Lys Gln Leu Ser Ile Leu Ala Cys Ala Gly Ile Thr Phe
    130                 135                 140

Ile Ser Ser Val Leu Ile Val Ser Val Ser Tyr Met Phe Ile Ile Ser
145                 150                 155                 160

Ala Ile Leu Arg Met Arg Ser Ala Glu Gly Arg Arg Lys Ala Phe Ser
                165                 170                 175

Thr Cys Ser Ser His Met Met Ala Val Ser Ile Phe Tyr Gly Thr Leu
            180                 185                 190

Ile Phe Met Tyr Leu Gln Pro Ser Ser Asp His Ser Leu Asp Thr Asp
        195                 200                 205

Lys Met Ala Ser Val Phe Tyr Thr Val Ile Ile Pro Met Leu Asn
    210                 215                 220
```

<210> SEQ ID NO 39
<211> LENGTH: 669
<212> TYPE: DNA
<213> ORGANISM: Mus musculus
<220> FEATURE:
<223> OTHER INFORMATION: PCR primer

<400> SEQUENCE: 39

```
agtcacttgt ccttcattga catgatgtac atctcaacca ttgtgcccaa aatgctagtt     60
gattatcttc tagggcaaag gactatttcc tttgtgggat gcacagctca acactttcta    120
tacctcaccc tggtgggagc cgagttcttt cttctgggcc tcatggctta tgatcgttat    180
```

```
gtggccatct gcaacccact gaggtaccct gtcctcatga gccgccggat ctgttggatt        240
atcatagcag gctcctggtt tgggggatct ttggatggct tcctcctcac tccaatcacc        300
atgagttttc ctttctgtag atcacgagag attaaccact tcttctgtga ggcacctgct        360
gtgctgaagt tggcatgtgc agacacagcc ctctatgaga cggtgatgta tgtgtgctgc        420
gttctgatgc tgttgattcc tttctctgtg gttatctcat cctatgcgcg gattctggcc        480
actgtctacc atatgagctc tgtggaagga aggaagaaag cgtttgctac ctgctcgtct        540
cacatgactg tggtaacctt gttttatggg gctgccatat acacctatat ggtaccacac        600
tcttaccatt ccccatccca agacaaaatt ttttctgtgt tctataccat tctcacaccc        660
atgctgaac                                                                669
```

<210> SEQ ID NO 40
<211> LENGTH: 223
<212> TYPE: PRT
<213> ORGANISM: Mus musculus
<220> FEATURE:
<223> OTHER INFORMATION: PCR primer

<400> SEQUENCE: 40

```
Ser His Leu Ser Phe Ile Asp Met Met Tyr Ile Ser Thr Ile Val Pro
  1               5                  10                  15

Lys Met Leu Val Asp Tyr Leu Leu Gly Gln Arg Thr Ile Ser Phe Val
             20                  25                  30

Gly Cys Thr Ala Gln His Phe Leu Tyr Leu Thr Leu Val Gly Ala Glu
         35                  40                  45

Phe Phe Leu Leu Gly Leu Met Ala Tyr Asp Arg Tyr Val Ala Ile Cys
     50                  55                  60

Asn Pro Leu Arg Tyr Pro Val Leu Met Ser Arg Arg Ile Cys Trp Ile
 65                  70                  75                  80

Ile Ile Ala Gly Ser Trp Phe Gly Gly Ser Leu Asp Gly Phe Leu Leu
                 85                  90                  95

Thr Pro Ile Thr Met Ser Phe Pro Phe Cys Arg Ser Arg Glu Ile Asn
            100                 105                 110

His Phe Phe Cys Glu Ala Pro Ala Val Leu Lys Leu Ala Cys Ala Asp
        115                 120                 125

Thr Ala Leu Tyr Glu Thr Val Met Tyr Val Cys Val Leu Met Leu
    130                 135                 140

Leu Ile Pro Phe Ser Val Val Ile Ser Ser Tyr Ala Arg Ile Leu Ala
145                 150                 155                 160

Thr Val Tyr His Met Ser Ser Val Glu Gly Arg Lys Lys Ala Phe Ala
                165                 170                 175

Thr Cys Ser Ser His Met Thr Val Val Thr Leu Phe Tyr Gly Ala Ala
            180                 185                 190

Ile Tyr Thr Tyr Met Val Pro His Ser Tyr His Ser Pro Ser Gln Asp
        195                 200                 205

Lys Ile Phe Ser Val Phe Tyr Thr Ile Leu Thr Pro Met Leu Asn
    210                 215                 220
```

<210> SEQ ID NO 41
<211> LENGTH: 669
<212> TYPE: DNA
<213> ORGANISM: Mus musculus
<220> FEATURE:
<223> OTHER INFORMATION: PCR primer

<400> SEQUENCE: 41

```
tgcaacttag cgaccatgga tattatctgc acctcctctg tactgcccaa ggcgctggtt      60
ggtctactgt ctgaggaaaa caccatcccc ttcaaagggt gcatgactca gctcttcttt     120
cttgtgtggt ctggatcctc tgagctgctg ctgctcacag tcatggccta tgaccgctat     180
gtggccatct gtttgcccct gcattacagc tctaggatga gtccacagct ctgtgggacc     240
tttgccgtgg gtgtatggtc catctgcgca ctaaatgcat ctatcaacac tggtctgatg     300
acacggctgt cattctgtgg ccccaaggtc atcacccact tcttctgtga gattccccca     360
ctcctcctgc tctcctgtag tcctacatat ataaatagcg ttatgactct tgtggcagat     420
gccttttatg gaggcatcaa ttttttactt accttgctat cctatggctg catcattgcc     480
agcatcctgc gcatgcgttc tgctgagggc aagaggaagg ccttttctac ctgctcatcc     540
cacctcatcg tggtctctgt gtactactca tctgtgttct gtgcctatat cagtcctggt     600
tccagctaca gcccagaaag aagcaaattt acctcggttt tgtactcagt cctcagccca     660
accctcaac                                                             669
```

<210> SEQ ID NO 42
<211> LENGTH: 223
<212> TYPE: PRT
<213> ORGANISM: Mus musculus
<220> FEATURE:
<223> OTHER INFORMATION: PCR primer

<400> SEQUENCE: 42

```
Cys Asn Leu Ala Thr Met Asp Ile Ile Cys Thr Ser Ser Val Leu Pro
  1               5                  10                  15

Lys Ala Leu Val Gly Leu Leu Ser Glu Glu Asn Thr Ile Pro Phe Lys
             20                  25                  30

Gly Cys Met Thr Gln Leu Phe Phe Leu Val Trp Ser Gly Ser Ser Glu
         35                  40                  45

Leu Leu Leu Leu Thr Val Met Ala Tyr Asp Arg Tyr Val Ala Ile Cys
     50                  55                  60

Leu Pro Leu His Tyr Ser Ser Arg Met Ser Pro Gln Leu Cys Gly Thr
 65                  70                  75                  80

Phe Ala Val Gly Val Trp Ser Ile Cys Ala Leu Asn Ala Ser Ile Asn
                 85                  90                  95

Thr Gly Leu Met Thr Arg Leu Ser Phe Cys Gly Pro Lys Val Ile Thr
            100                 105                 110

His Phe Phe Cys Glu Ile Pro Pro Leu Leu Leu Leu Ser Cys Ser Pro
        115                 120                 125

Thr Tyr Ile Asn Ser Val Met Thr Leu Val Ala Asp Ala Phe Tyr Gly
    130                 135                 140

Gly Ile Asn Phe Leu Leu Thr Leu Leu Ser Tyr Gly Cys Ile Ile Ala
145                 150                 155                 160

Ser Ile Leu Arg Met Arg Ser Ala Glu Gly Lys Arg Lys Ala Phe Ser
                165                 170                 175

Thr Cys Ser Ser His Leu Ile Val Val Ser Val Tyr Tyr Ser Ser Val
            180                 185                 190

Phe Cys Ala Tyr Ile Ser Pro Gly Ser Ser Tyr Ser Pro Glu Arg Ser
        195                 200                 205

Lys Phe Thr Ser Val Leu Tyr Ser Val Leu Ser Pro Thr Leu Asn
    210                 215                 220
```

<210> SEQ ID NO 43

```
<211> LENGTH: 675
<212> TYPE: DNA
<213> ORGANISM: Mus musculus
<220> FEATURE:
<223> OTHER INFORMATION: PCR primer

<400> SEQUENCE: 43
gccaacctct ccagtgtcga cattagtgct ccatctgtca ttgtcccaa ggcattggtg      60
aatcatatgt tgggaagcaa gtccatctct tacacggggt gtatgaccca gatctatttc    120
ttcatcacat tcaacaatat ggatggcttc ctcctgagtg tgatggccta tgaccgctat    180
gtggccatct gtcaccctct ccactacacc atgatgatga gacccagact ctgtgtcctc    240
ctggtggcca tatcatgggc catcacaaac ctgcatgctc tcttgcatac tctcctcatg    300
gttcgactca ccttctgttc cacaatgca gtgcaccact tcttctgtga ccctaccct      360
atcctgaagc tctcttgttc tgacaccttc atcaatgacc tgatggtctt caccattggt    420
ggattggtat ttatgactcc atttacatgc attattgttt cctatgccta catcttctct    480
aaggttctga agttaaaatc tgcccatgga ataaggaaag ccctgtcgac gtgtgggtct    540
cacctcactg tggtctccct cttctatggg gcgatcctgg catctatat gcacccttca     600
tctacataca cagtgcagga cacagtggcc accgtcatct tcacagtagt gacacccatg    660
gtcaacaccc tcaac                                                     675

<210> SEQ ID NO 44
<211> LENGTH: 222
<212> TYPE: PRT
<213> ORGANISM: Mus musculus
<220> FEATURE:
<223> OTHER INFORMATION: PCR primer

<400> SEQUENCE: 44

Ala Asn Leu Ser Ser Val Asp Ile Ser Ala Pro Ser Val Ile Val Pro
 1               5                  10                  15

Lys Ala Leu Val Asn His Met Leu Gly Ser Lys Ser Ile Ser Tyr Thr
                20                  25                  30

Gly Cys Met Thr Gln Ile Tyr Phe Phe Ile Thr Phe Asn Asn Met Asp
            35                  40                  45

Gly Phe Leu Leu Ser Val Met Ala Tyr Asp Arg Tyr Val Ala Ile Cys
        50                  55                  60

His Pro Leu His Tyr Thr Met Met Arg Pro Arg Leu Cys Val Leu
 65                  70                  75                  80

Leu Val Ala Ile Ser Trp Ala Ile Thr Asn Leu His Ala Leu Leu His
                85                  90                  95

Thr Leu Leu Met Val Arg Leu Thr Phe Cys Ser His Asn Ala Val His
                100                 105                 110

His Phe Phe Cys Asp Pro Tyr Pro Ile Leu Lys Leu Ser Cys Ser Asp
            115                 120                 125

Thr Phe Ile Asn Asp Leu Met Val Phe Thr Ile Gly Leu Val Phe
        130                 135                 140

Met Thr Pro Phe Thr Cys Ile Ile Val Ser Tyr Ala Tyr Ile Phe Ser
145                 150                 155                 160

Lys Val Leu Lys Leu Lys Ser Ala His Gly Ile Arg Lys Ala Leu Ser
                165                 170                 175

Thr Cys Gly Ser His Leu Thr Val Val Ser Leu Phe Tyr Gly Ala Ile
            180                 185                 190

Leu Gly Ile Tyr Met His Pro Ser Ser Thr Tyr Thr Val Gln Asp Thr
```

```
                195               200                205
Val Ala Thr Val Ile Phe Thr Val Val Thr Pro Met Val Asn
    210              215                 220
```

<210> SEQ ID NO 45
<211> LENGTH: 678
<212> TYPE: DNA
<213> ORGANISM: Mus musculus
<220> FEATURE:
<223> OTHER INFORMATION: PCR primer

<400> SEQUENCE: 45

```
agtcacttgg ccttcacgga catctctttc tcatctgtca cagctccaaa gatgctcatg     60
aatatgctga cacatagcca atccatctca catgctgggt gtgtttccca aatatatttt    120
ttcttattgt ttgggtgtat tgacaacttc cttctgactt ccatggccta tgacaggtat    180
gtggccatct gccaccctct gcattatacc actatcatga gtcaaagcct ctgtgttctg    240
ctagtgatgg tgtcctgggc attttcctct tctaatggcc ttgtgcatac tcttctcttt    300
gctcgtctct ctcttttag agacaacact gtccaccatt ttttctgtga tctctctgct    360
ttgctgaagc tgtccagctc agacactact atcaatgaac tagtaatcct cactttagca    420
gtggtggtca tcactgtacc attcatatgc atcctggttt cttatggcca catgggggcc    480
actatcctaa gaactccatc catcaagggt atctgcaaag ccttgtccac atgtggttct    540
catctctgtg tagtttcttt atattatgga gccattattg ggttatattt tttcccctcc    600
tccaataata ctaatgataa agatgtcata gtagctgtgt tgtacactgt ggttacaccc    660
atgctgaata ccctcaac                                                  678
```

<210> SEQ ID NO 46
<211> LENGTH: 223
<212> TYPE: PRT
<213> ORGANISM: Mus musculus
<220> FEATURE:
<223> OTHER INFORMATION: PCR primer

<400> SEQUENCE: 46

```
Ser His Leu Ala Phe Thr Asp Ile Ser Phe Ser Ser Val Thr Ala Pro
  1               5                  10                  15
Lys Met Leu Met Asn Met Leu Thr His Ser Gln Ser Ile Ser His Ala
             20                  25                  30
Gly Cys Val Ser Gln Ile Tyr Phe Phe Leu Leu Phe Gly Cys Ile Asp
         35                  40                  45
Asn Phe Leu Leu Thr Ser Met Ala Tyr Asp Arg Tyr Val Ala Ile Cys
     50                  55                  60
His Pro Leu His Tyr Thr Thr Ile Met Ser Gln Ser Leu Cys Val Leu
 65                  70                  75                  80
Leu Val Met Val Ser Trp Ala Phe Ser Ser Asn Gly Leu Val His
                 85                  90                  95
Thr Leu Leu Phe Ala Arg Leu Ser Leu Phe Arg Asp Asn Thr Val His
            100                 105                 110
His Phe Phe Cys Asp Leu Ser Ala Leu Leu Lys Leu Ser Ser Ser Asp
        115                 120                 125
Thr Thr Ile Asn Glu Leu Val Ile Leu Thr Leu Ala Val Val Val Ile
    130                 135                 140
Thr Val Pro Phe Ile Cys Ile Leu Val Ser Tyr Gly His Met Gly Ala
145                 150                 155                 160
```

Thr Ile Leu Arg Thr Pro Ser Ile Lys Gly Ile Cys Lys Ala Leu Ser
                165                 170                 175

Thr Cys Gly Ser His Leu Cys Val Val Ser Leu Tyr Tyr Gly Ala Ile
            180                 185                 190

Ile Gly Leu Tyr Phe Phe Pro Ser Ser Asn Asn Thr Asn Asp Lys Asp
        195                 200                 205

Val Ile Val Ala Val Leu Tyr Thr Val Thr Pro Met Leu Asn
    210                 215                 220

<210> SEQ ID NO 47
<211> LENGTH: 951
<212> TYPE: DNA
<213> ORGANISM: Mus musculus
<220> FEATURE:
<223> OTHER INFORMATION: PCR primer

<400> SEQUENCE: 47

| | | | | | |
|---|---|---|---|---|---|
| atggcgaaca | gcactactgt | tactgagttt | attttgctgg | ggctgtcaga | tgcctgtgag | 60 |
| ctgcaggtgc | tcatattcct | gggctttctc | ctgacctact | tcctcattct | gctgggaaac | 120 |
| ttcctcatca | tcttcatcac | ccttgtggac | aggcgccttt | acacccccat | gtattacttc | 180 |
| ctccgcaact | tgccatgct | ggagatctgg | ttcacctctg | tcatcttccc | caagatgcta | 240 |
| accaacatca | tcacaggaca | taagaccatc | tccctactag | gttgtttcct | ccaagcattc | 300 |
| ctctatttct | tccttggcac | cactgagttc | tttctactgg | cagtgatgtc | ctttgacagg | 360 |
| tatgtggcca | tttgtaaccc | tttgcgttat | gccaccatta | tgagcaaaag | agtctgtgtc | 420 |
| cagcttgtgt | tttgctcatg | gatgtctgga | ttgcttctca | tcatagttcc | tagttcaatt | 480 |
| gtatttcagc | agccattctg | tggcccaaac | atcattaatc | atttcttctg | tgacaacttt | 540 |
| ccacttatgg | aactcatatg | tgcagatact | agcctggtag | agttcctggg | ttttgttatt | 600 |
| gccaatttca | gctcctggg | cactctggct | gtgactgcca | cctgctatgg | ccacattctc | 660 |
| tataccattc | tacacattcc | ttcagccaag | gagaggaaga | aagccttctc | aacttgctcc | 720 |
| tctcatatta | ttgtggtgtc | tctcttctac | ggcagctgta | tcttcatgta | tgtccggtct | 780 |
| ggcaagaatg | gacaggggga | ggatcataac | aaggtggtgg | cattgctcaa | cactgtagtg | 840 |
| acacccacac | tcaaccccttt | catctacact | ctgaggaaca | gcaggtgaa | gcaggtattt | 900 |
| agggaacacg | taagcaagtt | ccaaaagttc | agccagacgt | gaaccctcaa | c | 951 |

<210> SEQ ID NO 48
<211> LENGTH: 313
<212> TYPE: PRT
<213> ORGANISM: Mus musculus
<220> FEATURE:
<223> OTHER INFORMATION: PCR primer

<400> SEQUENCE: 48

Met Ala Asn Ser Thr Thr Val Thr Glu Phe Ile Leu Leu Gly Leu Ser
 1               5                  10                  15

Asp Ala Cys Glu Leu Gln Val Leu Ile Phe Leu Gly Phe Leu Leu Thr
            20                  25                  30

Tyr Phe Leu Ile Leu Leu Gly Asn Phe Leu Ile Ile Phe Ile Thr Leu
        35                  40                  45

Val Asp Arg Arg Leu Tyr Thr Pro Met Tyr Tyr Phe Leu Arg Asn Phe
    50                  55                  60

Ala Met Leu Glu Ile Trp Phe Thr Ser Val Ile Phe Pro Lys Met Leu
65                  70                  75                  80

-continued

```
Thr Asn Ile Ile Thr Gly His Lys Thr Ile Ser Leu Leu Gly Cys Phe
            85                  90                  95

Leu Gln Ala Phe Leu Tyr Phe Phe Leu Gly Thr Thr Glu Phe Phe Leu
            100                 105                 110

Leu Ala Val Met Ser Phe Asp Arg Tyr Val Ala Ile Cys Asn Pro Leu
            115                 120                 125

Arg Tyr Ala Thr Ile Met Ser Lys Arg Val Cys Val Gln Leu Val Phe
            130                 135                 140

Cys Ser Trp Met Ser Gly Leu Leu Ile Ile Val Pro Ser Ser Ile
145                 150                 155                 160

Val Phe Gln Gln Pro Phe Cys Gly Pro Asn Ile Ile Asn His Phe Phe
            165                 170                 175

Cys Asp Asn Phe Pro Leu Met Glu Leu Ile Cys Ala Asp Thr Ser Leu
            180                 185                 190

Val Glu Phe Leu Gly Phe Val Ile Ala Asn Phe Ser Leu Leu Gly Thr
            195                 200                 205

Leu Ala Val Thr Ala Thr Cys Tyr Gly His Ile Leu Tyr Thr Ile Leu
            210                 215                 220

His Ile Pro Ser Ala Lys Glu Arg Lys Lys Ala Phe Ser Thr Cys Ser
225                 230                 235                 240

Ser His Ile Ile Val Val Ser Leu Phe Tyr Gly Ser Cys Ile Phe Met
            245                 250                 255

Tyr Val Arg Ser Gly Lys Asn Gly Gln Gly Glu Asp His Asn Lys Val
            260                 265                 270

Val Ala Leu Leu Asn Thr Val Thr Pro Thr Leu Asn Pro Phe Ile
            275                 280                 285

Tyr Thr Leu Arg Asn Lys Gln Val Lys Gln Val Phe Arg Glu His Val
            290                 295                 300

Ser Lys Phe Gln Lys Phe Ser Gln Thr
305                 310
```

<210> SEQ ID NO 49
<211> LENGTH: 6
<212> TYPE: PRT
<213> ORGANISM: Mus musculus
<220> FEATURE:
<223> OTHER INFORMATION: PCR primer

<400> SEQUENCE: 49

```
Leu Phe Leu Leu Tyr Leu
1               5
```

<210> SEQ ID NO 50
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(9)
<223> OTHER INFORMATION: Xaa = Any Amino Acid

<400> SEQUENCE: 50

```
Met Arg Xaa Asp Arg Tyr Val Ala Ile
1               5
```

<210> SEQ ID NO 51
<211> LENGTH: 20
<212> TYPE: DNA

<210> SEQ ID NO 51
<211> LENGTH: 20
<212> TYPE: DNA
<213> ORGANISM: Artificial Sequence
<220> FEATURE:
<223> OTHER INFORMATION: consensus sequence

<400> SEQUENCE: 51
atggsctwtg accghtwygt					20

<210> SEQ ID NO 52
<211> LENGTH: 6
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(6)
<223> OTHER INFORMATION: Xaa = Any Amino Acid

<400> SEQUENCE: 52

Thr Cys Xaa Ser His Leu
 1               5

<210> SEQ ID NO 53
<211> LENGTH: 17
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)...(17)
<223> OTHER INFORMATION: n = A,T,C or G

<400> SEQUENCE: 53
agrtgnswns crcangt					17

<210> SEQ ID NO 54
<211> LENGTH: 374
<212> TYPE: DNA
<213> ORGANISM: Artificial Sequence
<220> FEATURE:
<223> OTHER INFORMATION: hyrbid receptor

<400> SEQUENCE: 54
ggatccgggt tcgcgccgcc ggcgggcagc cgcaagggcc gcagccatga acgggaccga	60 gggcccaaac ttctacgtgc ctttctccaa caagacgggc gtggtggaat tccccggtca	120 gaactacagc accatatcag aatttatcct ctttggtttc tcagccttcc cacaccagat	180 gctccctgct ctgttcctgc tctacttgct gatgtatttg ttcactcttc tggggaacct	240 ggtcatcatg gctgctatct ggacagaaca tagactgcag acaccatcc ggaaaggagc	300 tgaagaatgc tataattaaa agcttccaca ggaatgtctg tcaacaaagt atctaagtgt	360 cagttctgtc taga					374

<210> SEQ ID NO 55
<211> LENGTH: 101
<212> TYPE: PRT
<213> ORGANISM: Artificial Sequence
<220> FEATURE:
<223> OTHER INFORMATION: hybrid receptor

<400> SEQUENCE: 55

Met Asn Gly Thr Glu Gly Pro Asn Phe Tyr Val Pro Phe Ser Asn Lys
 1               5                  10                  15

Thr Gly Val Val Glu Phe Pro Gly Gln Asn Tyr Ser Ser Thr Ile Ser

```
                20              25              30
Glu Phe Ile Leu Phe Gly Phe Ser Ala Phe Pro His Gln Met Leu Pro
            35              40              45

Ala Leu Phe Leu Leu Tyr Leu Leu Met Tyr Leu Phe Thr Leu Leu Gly
    50              55              60

Asn Leu Val Ile Met Ala Ala Ile Trp Thr Glu His Arg Leu Gln Ser
65              70              75              80

Gly Lys Glu Leu Lys Asn Ala Ile Ile Lys Ser Phe His Arg Asn Val
                85              90              95

Cys Gln Gln Ser Ile
            100

<210> SEQ ID NO 56
<211> LENGTH: 6
<212> TYPE: PRT
<213> ORGANISM: Mus musculus
<220> FEATURE:
<221> NAME/KEY: VARIANT
<222> LOCATION: (4)...(4)
<223> OTHER INFORMATION: Xaa=Phe or Leu
<220> FEATURE:
<221> NAME/KEY: VARIANT
<222> LOCATION: (6)...(6)
<223> OTHER INFORMATION: Xaa=Phe or Leu

<400> SEQUENCE: 56

Pro Met Tyr Xaa Phe Xaa
1               5

<210> SEQ ID NO 57
<211> LENGTH: 6
<212> TYPE: PRT
<213> ORGANISM: Mus musculus
<220> FEATURE:
<221> NAME/KEY: VARIANT
<222> LOCATION: (2)...(2)
<223> OTHER INFORMATION: Xaa=Phe, Leu, Ile, or Val
<220> FEATURE:
<221> NAME/KEY: VARIANT
<222> LOCATION: (5)...(5)
<223> OTHER INFORMATION: Xaa=Ser or Thr

<400> SEQUENCE: 57

Pro Xaa Ile Tyr Xaa Leu
1               5
```

OLFACTORY RECEPTOR EXPRESSION LIBRARIES AND METHODS OF MAKING AND USING THEM

This application is a divisional of prior U.S. patent application Ser. No. 09/465,901 filed Dec. 17, 1999, now U.S. Pat. No. 6,492,143, which claims priority to U.S. Provisional Application No. 60/112,605 filed Dec. 17, 1998.

FIELD OF THE INVENTION

This invention generally pertains to the fields of cell biology and medicine. In particular, this invention provides novel libraries of nucleic acids encoding odorant/ligand-binding domains. Also provided are libraries of hybrid 7-transmembrane olfactory receptors comprising these odorant ligand-binding domains. The compositions and methods of the invention can be used to identify novel ligand-binding domains for olfactory neuron odorant receptors and their ligands. Thus, the compositions and methods of the invention can be used to generate novel odorants and to manipulate an animal's olfactory response.

BACKGROUND OF THE INVENTION

A better understanding of the vertebrate olfactory system would provide improved means to manipulate this process and possibly prevent disease or injury. For example, means to manipulate human olfactory neuron odorant receptors from healthy individuals and from individuals with neuropsychiatric illnesses would offer systems for testing possible odorant/ligands for therapeutic and toxic effects. However, our ability to detect and discriminate between the thousands of beneficial or toxic odorants is complicated by the fact that odorant receptors belong to a multigene family with at least 500 to 1000 members. Furthermore, each olfactory receptor neuron may express only one, or at most a few, of these olfactory receptors. Any given olfactory neuron cell can respond to a small, arbitrary set of odorant-ligands. Odorant discrimination for a given neuron may depend on the ligand specificity of the one or few receptors it expresses. Thus, given this systems' complexity, information about odorant/ligand-receptor recognition remains meager.

To analyze odorant/ligand-receptor interactions and their effects on cell physiology, it is first necessary to identify specific odorant/ligand(s) and the olfactory receptors to which they specifically bind. Such analysis requires isolation and expression of olfactory receptor polypeptides. However, despite the fact that many putative olfactory receptors have been cloned, only limited progress has been made in the functional expression of these receptors because present systems fail to efficiently translocate these 7-transmembrane proteins to the plasma membrane. This may be because olfactory receptors are a subclass of 7-transmembrane-domain receptors. For example, expression of one rat olfactory receptor in insect cells resulted in only a modest elevation in second messengers when exposed to a mixture of odorants; responses to single compounds were not seen (Raming (1993) Nature 361:353–356). The present invention addresses these and other needs.

SUMMARY OF THE INVENTION

The present invention provides novel compositions and methods to generate great numbers, or libraries, of odorant receptor ligand-binding regions. Also provided are novel chimeric olfactory receptors that incorporate these libraries of odorant binding domains. The present invention also provides novel compositions and methods to efficiently translocate polypeptides to the plasma membrane surface. Another aspect of the invention is based on the surprising discovery of a peptide domain that, when incorporated into a polypeptide, can with great efficiency "chaperone" or translocate the hybrid protein to the cell plasma membrane. Combining these two aspects of the invention also provides expression vectors and cells that efficiently express these recombinant proteins. Cells and transgenic animals efficiently expressing libraries of hybrid olfactory receptors can be used for screening potential beneficial and toxic odorant molecules.

The invention provides an amplification primer sequence pair for amplifying a nucleic acid encoding an olfactory receptor ligand-binding region comprising a first primer comprising a sequence 5'-GGGGTCCGGAG(A/G)(C/G)(A/G)TA(A/G/T)AT(A/G/P)A(A/G/P)(A/G/P)GG-3' (SEQ ID NO:1) and a second primer comprising a sequence 5'-GGGGCTGCAGACACC(A/C/G/T)ATGTA(C/T)(C/T)T(A/C/G/T)TT(C/T)(C/T)T-3' (SEQ ID NO:2). When used to amplify olfactory receptor nucleic acid sequences, it typically amplifies the receptor ligand-binding region comprising olfactory receptor transmembrane (TM) domains II through VII.

The invention also provides a method for generating nucleic acid sequence that encodes a ligand-binding region of an olfactory receptor, the method comprising amplification of a nucleic acid using the primer pair SEQ ID NO:1 and SEQ ID NO:2. In this method the amplified nucleic acid can be genomic DNA, mRNA or cDNA derived from olfactory neurons or olfactory epithelium. The amplification can be by polymerase chain reaction (PCR), wherein the PCR amplification comprises the following conditions and steps in the following order: about one cycle at about 94° C. for about 2 min; and about 30 cycles of about 45° C. to about 65° C. for about 1 min, followed by about 72° C. for about one min. followed by about 94° C. for about 1 min. The PCR amplification protocol can further comprise the following conditions and steps in the following order: about one cycle of about 45° C. to about 65° C. for about 10 min; and about one cycle of about 72° C. for about 10 min.

Also provides is a kit for amplification of olfactory receptor sequences comprising primer pairs that can amplify olfactory receptor transmembrane domain regions II through VII, II through VI, III through VII, or III through VI, e.g., SEQ ID NO:1 and SEQ ID NO:2 to amplify TM II through VII.

The invention also provides a library of olfactory receptor ligand-binding regions consisting essentially of olfactory receptor transmembrane domain regions II through VII, II through VI, III through VII, or III through VI, including partial domains, or a combination of domain sequences. The library of the olfactory receptor ligand-binding regions can be generated by PCR using degenerate primer pairs.

Also provided is a library of chimeric nucleic acid sequences comprising the following domains in 5' to 3' order: a nucleic acid encoding an amino terminal plasma membrane translocation domain; a nucleic acid encoding a first transmembrane domain; and a nucleic acid encoding an olfactory receptor ligand-binding region, wherein the chimeric nucleic acid sequence encodes a 7-transmembrane polypeptide that can transverse a plasma membrane seven times. The amino terminal plasma membrane translocation domain comprises an amino acid sequence as set forth in SEQ ID NO:3 (and encoded by a subsequence of SEQ ID NO:6): 5'-

```
5'-GGATCCGGGTTCGCGCCGCCGGCGGGCAGCCGCAAGGGCCGCAGCCATGAACGGGACCGAGGGC    (SEQ ID NO:6)
                                                 M   N   G   T   E   G  (SEQ ID NO:3)

CCAAACTTCTACGTGCCTTTCTCCAACAAGACGGGCGTGGTGGAATTC-3'
 P   N   F   Y   V   P   F   S   N   K   T   G   V   V
```

In alternative embodiments, the nucleic acid encoding the first transmembrane domain can be just a polynucleotide sequence encoding SEQ ID NO:3, or, SEQ ID NO:6 (including 45 nucleotides upstream of the initiation codon) or a subsequence thereof.

The first transmembrane receptor of the sequences of the library can be a 7-transmembrane receptor region I domain, or subsequence thereof, e.g., the sequence between the Eco R1 and Pst 1 sites of the M4-chimeric olfactory receptor of the invention (SEQ ID NO:4), as schematically represented in FIG. 1A; the full length sequence of the hybrid receptor has an amino acid sequence as set forth in SEQ ID NO:55, a nucleic acid that can encode this protein is SEQ ID NO:54, described below.

The olfactory receptor ligand-binding regions of the library can comprise olfactory receptor transmembrane domain regions II through VII, II through VI, III through VII, or III through VI, or a combination thereof. These olfactory receptor ligand-binding regions can be generated by amplification, e.g., PCR, using degenerate primer pairs. The library's nucleic acid sequence encoding transmembrane domain regions II through VII can generated by PCR amplification of nucleic acid using a first primer comprising a sequence 5'-GGGGTCCGGAG(A/G)(C/G)(A/G)TA(A/G/T)AT(A/G/P)A(A/G/P)(A/G/P)GG-3' (SEQ ID NO:1) and a second primer comprising a sequence 5'-GGGGCTGCA-GACACC(A/C/G/T)ATGTA(C/T)(C/T)T(A/C/G/T)TT(C/T)(C/T)T-3' (SEQ ID NO:2). The library can be generated from PCR-amplified nucleic acid isolated as or derived from genomic DNA, mRNA or cDNA derived from olfactory neurons or olfactory epithelium.

Exemplary ligand-binding regions comprising transmembrane domains II through VII ca be an amino acid sequence encoded by a nucleic acid selected from the group consisting of SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 and SEQ ID NO:47, or an amino acid sequence selected from the group consisting of SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48.

To generate the nucleic acids of the library, PCR amplification can comprise the following conditions and steps in the following order: about one cycle at about 94° C. for about 2 min; about 30 cycles of about 55° C. for about 1 min, followed by about 72° C. for about one min. followed by about 94° C. for about 1 min; about one cycle of about 55° C. for about 10 min; and about one cycle of about 72° C. for about 10 min.

The library can further comprise a carboxy terminal 7-transmembrane receptor transmembrane region VII domain or subsequence thereof, e.g., the sequence between the Bsp E1 and Xba 1 sites of the M4-chimeric olfactory receptor of the invention (SEQ ID NO:6), as schematically represented in FIG. 1A; the full length sequence of the hybrid receptor has an amino acid sequence as set forth in SEQ ID NO:55, a nucleic acid that can encode this protein is SEQ ID NO:54.

The library of nucleic acid sequences can also comprise the following domains in 5' to 3' order: a nucleic acid encoding an amino terminal plasma membrane translocation domain comprising a sequence as set forth in SEQ ID NO:3, a nucleic acid encoding a transmembrane region I domain comprising a sequence as set forth in SEQ ID NO:4, a nucleic acid sequence generated by polymerase chain reaction (PCR) amplification of mRNA or cDNA derived from olfactory epithelium using a first primer comprising a sequence 5'-GGGGTCCGGAG(A/G)(C/G)T(A/G)A(A/G/T)AT(A/G/P)A(A/G/P)(A/G/P)GG-3' (SEQ ID NO:1) and a second primer comprising a sequence 5'-GGGGCTGCA-GACACC(A/C/G/T)ATGTA(C/T)C/T)T(A/C/G/T)TT(C/T)C/T)T-3' (SEQ ID NO:2), and a nucleic acid encoding a 7-transmembrane receptor transmembrane region VII domain comprising a sequence as set forth in SEQ ID NO:6.

Also provided are expression vectors (e.g., plasmids, viruses) comprising a nucleic acid sequence derived from the libraries of nucleic acid sequences of the invention. Transformed or isolated infected cells comprising a nucleic acid sequence derived from a library of nucleic acid sequences of the invention or an expression vector of the invention are also provided. Transgenic non-human animals comprising a nucleic acid sequence derived from a library of nucleic acid of the invention or an expression vector of the invention are also provided. In the transgenic animal, the expression vector can be a mammalian expression vector that can be expressed in olfactory epithelium or olfactory neurons.

The invention also provides a library of recombinant polypeptides translated or derived from the library of nucleic acids of the invention. Also provided are polypeptides isolated or derived from the library of polypeptides of the invention.

Also provided are methods of determining whether a test compound specifically binds to a mammalian olfactory receptor comprising the following steps: expressing a nucleic acid derived from a nucleic acid library of the invention under conditions permissive for translation of the nucleic acid to a receptor polypeptide; contacting the translated polypeptide with the test compound; and determining whether the test compound specifically binds to the polypeptide.

Also provided are methods of determining whether a test compound specifically binds to a mammalian olfactory transmembrane receptor comprising the following steps: contacting a cell stably or transiently transfected with a nucleic acid derived from a nucleic acid library of the invention; culturing the cell under conditions permissive for translation of the nucleic acid to a receptor polypeptide with the test compound; and determining whether the test compound specifically binds to the receptor polypeptide. In this method, the receptor polypeptide can be expressed as a transmembrane receptor with a ligand-binding site on the cell's plasma membrane outer surface. The specific binding of the test compound to the polypeptide can be determined by measuring a change in the physiologic activity of the cell, wherein a change in the cell's activity measured in the presence of the test compound compared to the cell's activity in the absence of the test compound provides a determination that the test compound specifically binds to the polypeptide. The measured cell activity can be a change in the calcium ion ($Ca^{2+}$) or cAMP concentration in the cell, which can be measured by loading the cell with a calcium ion-sensitive fluorescent dye before contacting the cell with the test compound. In this method any cell can be used, e.g., a human cell or a *Xenopus* oocyte.

Also provided are methods of determining whether a test compound specifically binds to a mammalian olfactory transmembrane receptor polypeptide in vivo comprising the following steps: contacting a non-human animal stably or transiently infected with a nucleic acid derived from the library of the invention or an expression vector of the invention with the test compound; and determining whether the animal reacts to the test compound by specifically binding to the receptor polypeptide, wherein the specific binding of the test compound to the polypeptide is determined by measuring a change in a physiologic activity of the animal, wherein a change in a receptor-encoding vector-infected animal's activity measured in the presence of the test compound compared to a bare vector-infected animal's activity in the presence of the test compound provides a determination that the test compound specifically binds to the mammalian olfactory transmembrane receptor polypeptide. In this method, the measured physiologic activity can be measured by an electroolfactogram. The vector can be a recombinant virus, e.g., an adenovirus expression vector.

The invention also provides a method of determining whether a test compound is neurotoxic to an olfactory neuron expressing an olfactory transmembrane receptor polypeptide comprising the following steps: contacting an olfactory neuron cell stably or transiently infected with a nucleic acid derived from a library of olfactory receptor ligand-binding regions consisting essentially of olfactory receptor transmembrane domain regions II through VII, II through VI, III through VII, or III through VI or a library of chimeric nucleic acid sequences comprising the following domains in 5' to 3' order: a nucleic acid encoding an amino terminal plasma membrane translocation domain; a nucleic acid encoding a first transmembrane domain; and a nucleic acid encoding an olfactory receptor ligand-binding region, wherein the chimeric nucleic acid sequence encodes a 7-transmembrane polypeptide that can traverse a plasma membrane seven times or an expression vector comprising a nucleic acid sequence derived from one of the above libraries with the test compound; and measuring the physiologic activity of the cell, wherein a change in the cell's activity measured in the presence of the test compound compared to the cell's activity in the absence of the test compound provides a determination that the test compound is toxic. In this method toxicity can be indicated by abnormal calcium ion, cAMP or plasma membrane homeostasis.

Also provided are peptide domains for the efficient translocation of a newly translated protein to a plasma membrane comprising an amino acid sequence as set forth in SEQ ID NO:3 or an amino acid sequence having conservative amino acid residue substitutions based on SEQ ID NO:3. Translocation domains within the scope of the invention include amino acid sequences functionally equivalent to the exemplary translocation domain of the invention SEQ ID NO:3. The peptide translocation domain can be at least about 20 amino acids in length, at least about 30 amino acids in length or at least about 40 amino acids in length. The peptide translocation domain can have a sequence as set forth in SEQ ID NO:3, or, be encoded by a nucleic acid comprising a sequence as set forth in SEQ ID NO:6. The newly translated protein can be a transmembrane protein, e.g., a 7-transmembrane protein receptor, e.g., an olfactory receptor.

The invention also provides a hybrid (chimeric) polypeptide comprising an amino terminal amino acid sequence comprising a peptide translocation domain of the invention and a second polypeptide sequence, wherein the second polypeptide sequence is not a rhodopsin polypeptide sequence. The second polypeptide sequence can be a transmembrane protein, e.g., a 7-transmembrane protein receptor, e.g., an olfactory receptor. Also provides are isolated or recombinant nucleic acid sequences encoding these hybrid polypeptides. For example, an exemplary chimeric polypeptide of the invention and a polynucleotide that encodes this hybrid, described in the Example below and schematically represented in FIG. 1A as the insert from BamH1 to XbaI, have the amino acid (SEQ ID NO:55) and nucleic acid (SEQ ID NO:54) sequence, respectively (restriction enzyme sites are also indicated):

```
            BamHI
GGATCCGGGTTCGCGCCGCCGGCGGGCAGCCGCAAGGGCCGCAGCCATGAACGGGACCGAGGGC      (SEQ ID NO:54)
                                              M  N  G  T  E  G        (SEQ ID NO:55)

EcoRI
CCAAACTTCTACGTGCCTTTCTCCAACAAGACGGGCGTGGTGGAATTCCCCGGTCAGAACTACA
 P  N  F  Y  V  P  F  S  N  K  T  G  V  V  E  F  P  G  Q  N  Y    S

GCACCATATCAGAATTTATCCTCTTTGGTTTCTCAGCCTTCCCACACCAGATGCTCCCTGCTCT
 S  T  I  S  E  F  I  L  F  G  F  S  A  F  P  H  Q  M  L  P  A  L

GTTCCTGCTCTACTTGCTGATGTATTTGTTCACTCTTCTGGGGAACCTGGTCATCATGGCTGCT
   F  L  L  Y  L  L  M  Y  L  F  T  L  L  G  N  L  V  I  M  A  A

PstI          BspEI
ATCTGGACAGAACATAGACTGCAGACACCCATCCGGAAAGGAGCTGAAGAATGCTATAATTAAA
 I  W  T  E  H  R  L  Q          S  G  K  E  L  K  N  A  I  I  K

XbaI
AGCTTCCACAGGAATGTCTGTCAACAAAGTATCTAAGTGTCAGTTCTGTCTAGA
 S  F  H  R  N  V  C  Q  Q  S  I  STOP
```

A further understanding of the nature and advantages of the present invention is realized by reference to the remaining portions of the specification, the figures and claims.

All publications, GenBank deposited sequences, ATCC deposits, patents and patent applications cited herein are hereby expressly incorporated by reference for all purposes.

DETAILED DESCRIPTION OF THE INVENTION

Figure 1:
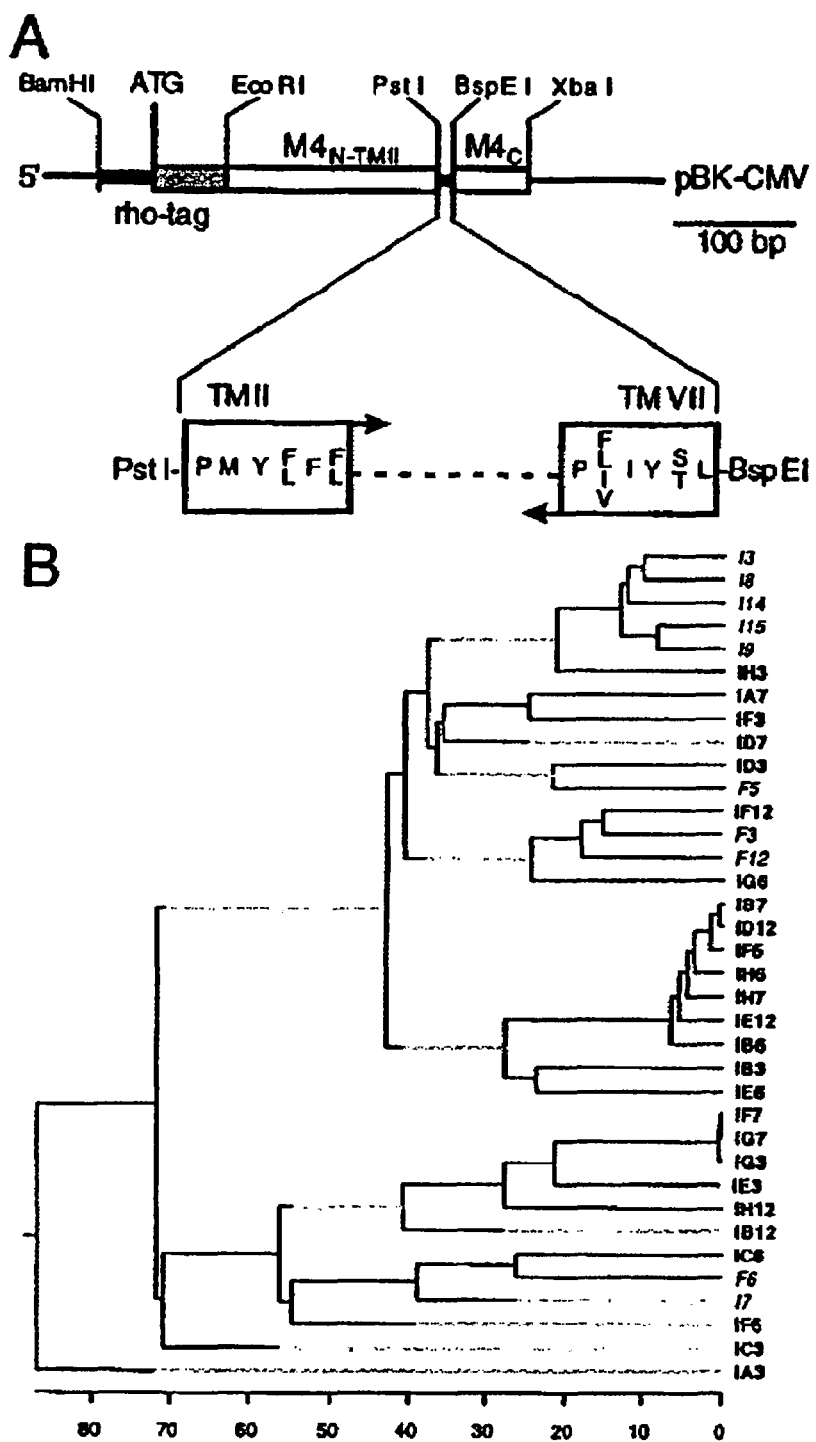
FIG. 1A shows a schematic of a mammalian expression construct of the invention comprising a translocation domain of the invention and an odorant/ligand-binding domain generated by degenerate PCR primers, as described in detail in Example 1, below.
FIG. 1B shows a similarity dendrogram. New members of the olfactory receptor family are shown in bold-type. Previously cloned olfactory receptors are shown in italics.

The present invention provides novel compositions and methods to efficiently translocate newly translated polypeptides to the plasma membrane surface. This aspect of the invention is based on the surprising discovery of peptide domains (e.g., SEQ ID NO:3) that, when incorporated into the amino terminus of a polypeptide coding sequence, can with great efficiency "chaperone" or "translocate" the hybrid ("fusion") protein to the cell plasma membrane. This "translocation domain" was initially derived from the amino terminus of the human rhodopsin receptor polypeptide, a 7-transmembrane receptor. Thus, the translocation domain of the invention is particularly efficient in translocating 7-transmembrane fusion proteins to the plasma membrane. For example, the mouse olfactory receptor M4 (see, e.g., Qasba (1998) J. Neurosci. 18:227–236) expressed in a mammalian cell line is inefficiently translocated to the cell. In contrast, when a translocating domain of the invention (SEQ ID NO:3) was spliced to the amino terminus of the M4 olfactory receptor polypeptide, cell surface expression of the newly translated protein increased from undetectable levels to 10% or more of the total expressed protein (as determined by confocal microscopic imaging with antibodies that recognize the carboxyl terminus of the M4 receptor). Furthermore, subsequent functional expression studies demonstrated that no responses could be observed upon addition of extracellular ligand unless the translocation domain of the invention (SEQ ID NO:3) was included to effect surface localization.

The invention also provides novel means to generate libraries of odorant/ligand-binding regions of olfactory receptor proteins. Great numbers of these ligand-regions can be generated by amplification (e.g., by polymerase chain reaction (PCR)) of nucleic acid from olfactory neurons and epithelium using degenerate primer pairs. The primer pairs selectively amplify the odorant/ligand-binding regions of olfactory receptor proteins. The odorant/ligand-binding regions can comprise transmembrane domain II through VII, III through VII, III through VI, II through VI, or combinations or variation thereof, of the 7-transmembrane olfactory receptor (see below for detailed discussion). Thus, amplification of, e.g., genomic DNA, or message or cDNA from olfactory neurons, using the degenerate primers of the invention can generate great numbers, or "libraries," of odorant/ligand-binding region encoding nucleic acid.

The odorant/ligand-binding region-amplifying degenerate primers of the invention are at least about 17 base pair residues in length. Amplification conditions can vary; however, lower temperature conditions (e.g., below about 55° C., usually not lower than about 45° C.) will generate libraries of greater complexity and higher temperatures (e.g., over about 55° C.) will generate libraries of less complexity.

For screening and identification of odorant/ligands that specifically bind to the domains encoded by the nucleic acid "libraries" of the invention, the amplified sequences can be recombinantly spliced into a "framework" polypeptide that is expressed on the cell surface. If functional studies (including, e.g., cell signaling responses, e.g., calcium transients) are desired, 7-membrane polypeptide coding sequences are used as "donor" regions. In this scheme, the "donor" 7-membrane polypeptide provides the coding sequence needed to complement the insert, i.e., a nucleic acid from an odorant/ligand-binding region library of the invention. For example, if the amplified odorant/ligand-binding region is equivalent to transmembrane domain II through VII, the "donor" provides transmembrane domain I; if the binding region is transmembrane domain III through VI, the "donor" provides the amino terminal transmembrane domain I and the carboxy terminal domain VII; and the like. Any 7-membrane polypeptide coding sequence can be used as "donor," including olfactory receptor polypeptide; however, some receptors which depend on long amino-terminal extensions for ligand recognition and binding (e.g., metabatropic glutamate, extracellular calcium sensors, GnRH and FSH peptide hormone receptors) may not produce functional receptors using this method.

These constructs can be cloned into expression systems, e.g., plasmids, vectors, viruses and the like. Any system can be used, from a minimal transcription unit (e.g., an expression cassette) to a recombinant virus capable of infecting an animal (e.g., an engineered adenovirus). These vectors can be used for functional expression assays in vitro or in vivo to screen large numbers of putative odorant/ligand molecules or to test for potential odorant toxicity.

The efficiency of the odorant-receptor screening systems of the invention are greatly increased by generating odorant receptor fusion proteins that can efficiently translocate to the plasma membrane. These hybrid receptors comprise the polypeptide translocating domains and the libraries of odorant/ligand-binding regions of the invention. With this scheme the invention provides an efficient means to generate and efficiently express thousands of olfactory receptor binding domains in functional cell and animal assays for the rapid screening of potential beneficial and toxic odorant/ligands.

Both in vitro and in vivo systems can be constructed and used in the methods of the invention. In vitro screening can include, e.g., liposome or lipid or planar membrane models. In vivo screening systems can include, e.g., use of human cells, e.g., olfactory neuron cell lines, or infection of animals (e.g., with virus with sequence encoding chimeric receptor) and transgenic animals that express the constructs of the invention. Adenovirus gene transfer vectors are particularly efficient for the transfer of nucleic acids encoding the hybrid olfactory receptor proteins of the invention to nasal/respiratory epithelium.

When human olfactory receptor nucleic acid is amplified, the in vitro models, cultured cells, and infected and transgenic animals can be used for screening large numbers of molecules for their potential as human odorants. The effect of an odorant on neuronal cell physiology can be also assessed. For example, the screening systems of the invention can be used to test whether an odorant/ligand may be potentially toxic (or beneficial) in humans. Any cell physiologic activity can be measured, e.g., cell death, cell growth, intracellular calcium ion changes, second messengers (e.g., G protein activation, cAMP increases), and the like. The effect of odorant/ligands on apoptotic mechanisms, neuronal growth characteristics (such as neuron population doubling time and length of processes), ion exchange and other measurable parameters can also be used to analyze their potential potency and toxicity.

Definitions:

The term "amplifying" and "amplification" as used herein incorporates its common usage and refers to the use of any suitable amplification methodology for generating or detecting recombinant or naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention (e.g., odorant/ligand binding sequences of the invention) in vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). Olfactory receptors belong to this family. 7-transmembrane receptor polypeptides have similar and characteristic primary, secondary and tertiary structures, as discussed in detail below.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

As used herein, "isolated," when referring to a molecule or composition, such as, e.g., an isolated infected cell comprising a nucleic acid sequence derived from a library of the invention, means that the molecule or composition (including, e.g., a cell) is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using any analytical chemistry technique, as described herein.

The term "library" means a preparation that is a mixture different nucleic acid or polypeptide molecules, such as the library of recombinantly generated olfactory receptor ligand binding domains generated by amplification of nucleic acid with degenerate primer pairs, e.g., SEQ ID NO:1 and SEQ ID NO:2, or an isolated collection of vectors that incorporate the amplified odorant/ligand binding domains of the invention, or a mixture of cells each randomly transfected with at least one vector of the invention.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogues of natural nucleotides. The term also encompasses nucleic-acid-like structures with synthetic backbones, see e.g., Oligonucleotides and Analogues, a Practical Approach, ed. F. Eckstein, Oxford Univ. Press (1991); Antisense Strategies, Annals of the N.Y. Academy of Sciences, Vol. 600, Eds. Baserga et al. (NYAS 1992); Milligan (1993) J. Med. Chem. 36:1923–1937; Antisense Research and Applications (1993, CRC Press), WO 97/03211; WO 96/39154; Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

The term "P" in the sequence is 5'-Dimethoxytrityl-N-benzoyl-2'-deoxy-Cytidine,3'-[(2-cyanoethyl)-(N,N-diisopropyl)]-phosphoramidite, or equivalent thereof. "P" can be purchased by, e.g., Glen Research, Sterling, Va., described as "dC-CE Phosphoramidite" catalog number 10-1010-xx.

The term "olfactory receptor ligand-binding region" or "olfactory receptor ligand-binding domain" means a sequence derived from an olfactory receptor that substantially incorporates transmembrane domains II to VII (TM II to VII). The domain may be capable of binding a ligand.

The term "plasma membrane translocation domain" or simply "translocation domain" means a polypeptide domain that is functionally equivalent to the exemplary translocation domain of the invention (SEQ ID NO:3). Exemplary amino terminal plasma membrane translocation domain SEQ ID NO:3 was initially derived from the rhodopsin receptor amino terminus. A protein (e.g., an olfactory receptor polypeptide) comprising SEQ ID NO:3 as an amino terminal translocating domain will be transported to the plasma membrane more efficiently than without the domain (e.g., as discussed above, M4 receptor expression increased from undetectable levels to at least 10% of the total expressed protein). "Functional equivalency" means the domain's ability and efficiency in translocating newly translated proteins to the plasma membrane as efficiently as exemplary SEQ ID NO:3 under similar conditions; relatively efficiencies can be measured (in quantitative terms) and compared, as described herein. Domains falling within the scope of the invention can be determined by routine screening for their efficiency in translocating newly synthesized polypeptides to the plasma membrane in a cell (mammalian, Xenopus, and the like) with the same efficiency as the twenty amino acid long translocation domain SEQ ID NO:3, as described in detail below.

The "translocation domain," odorant/ligand binding domains, and chimeric receptors compositions of the invention also include "analogs," or "conservative variants" and "mimetics" ("peptidomimetics") with structures and activity that substantially correspond to the exemplary sequences, such as the SEQ ID NO:3 translocation domain. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W.H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains or odorant-ligand binding domains or chimeric receptors of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(═O)—CH$_2$— for —C(═O)—NH—), aminomethylene (CH$_2$—NH), ethylene, olefin (CH═CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The term "transmembrane domain" means a polypeptide domain that can completely span the plasma membrane. The general secondary and tertiary structure of transmembrane domains, particular the seven transmembrane domains of 7-transmembrane receptors such as olfactory receptors, are well known in the art. Thus, primary structure sequence can be designed or predicted based on known transmembrane domain sequences, as described in detail, below. One such exemplary domain is the 7-transmembrane receptor transmembrane region I domain comprising a sequence as set forth in SEQ ID NO:4.

Generation and Genetic Engineering of Nucleic Acids

This invention provides novel PCR primers for the amplification of nucleic acids encoding olfactory receptor ligand binding regions and libraries of these nucleic acids. The invention also provides novel libraries of expression vectors that are used to infect or transfect cells for the functional expression of these libraries. As the genes and vectors of the invention can be made and expressed in vitro or in vivo, the invention provides for a variety of means of making and expressing these genes and vectors. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used for this invention. The invention can be practiced in conjunction with any method or protocol known in the art, which are well described in the scientific and patent literature.

General Techniques

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect or plant systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Amplification of Nucleic Acids

The invention provides oligonucleotide primers that can amplify nucleic acid encoding an olfactory receptor ligand-binding region. The nucleic acids of the invention can also be cloned or measured quantitatively using amplification techniques. Using the exemplary degenerate primer pair sequences of the invention (see below), the skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

Once amplified, the libraries can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites were chosen because they have a sequence that, when ligated, are "in-frame" with respect to the 7-membrane receptor "donor" coding sequence into which they are spliced (the odorant/ligand binding region-coding sequence is internal to the 7-membrane polypeptide, thus, if it is desired that the construct be translated downstream of a restriction enzyme splice site, out of frame results should be avoided; this may not be necessary if the inserted odorant/ligand binding domain comprises substantially most of the transmembrane VII region). The primers can be designed to retain the original sequence of the "donor" 7-membrane receptor (the Pst I and Bsp E1 sequence in the primers of the invention generate an insert that, when ligated into the Pst I/Bsp E1 cut vector, encode residues found in the "donor" mouse olfactory receptor M4 sequence). Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

Degenerate Primer Design

The primer pairs of the invention are designed to selectively amplify odorant/ligand-binding regions of olfactory receptor proteins. These domain regions may vary for different odorants; thus, what may be a minimal binding region for one odorant may be too limiting for a second potential ligand. Thus, the invention includes amplification of domain regions of different sizes comprising different domain structures; for example, transmembrane (TM) domains II through VII, III through VII, III through VI or II through VI, or variations thereof (e.g., only a subsequence of a particular domain, mixing the order of the domains, and the like), of a 7-transmembrane olfactory receptor. As domain structures and sequence of many 7-membrane proteins, particularly olfactory receptors, are known, the skilled artisan can readily select domain-flanking and internal domain sequences as model sequences to design degenerate amplification primer pairs. For example, a nucleic acid sequence encoding domain regions II through VII can be generated by PCR amplification using a primer pair SEQ ID NO:1 and SEQ ID NO:2 (see FIG. 1). To amplify a nucleic acid comprising transmembrane domain I (TM I) sequence, a degenerate primer can be designed from a nucleic acid that encodes the amino acid sequence LFLLYL 3' (SEQ ID NO:49). Such a degenerate primer can be used to generate a binding domain incorporating TM I through TM III, TM I through TM IV, TM I through TM V, TM I through TM VI or TM I through TM VII).

To amplify a nucleic acid comprising a transmembrane domain III (TM III) sequence, a degenerate primer (of at least about 17 residues) can be designed from a nucleic acid that encodes the amino acid sequence M(A/G)(Y/F)DRY-VAI 3' (SEQ ID NO:50 (encoded by a nucleic acid sequence such as 5'-ATGG(G/C)CT(A/T)TGACCG(C/A/T)T(AT)(C/T)GT-3' (SEQ ID NO:51)). Such a degenerate primer can be used to generate a binding domain incorporating TM III through TM IV, TM III through TM V, TM III through TM VI or TM III through TM VII.

To amplify transmembrane domain VI (TM VI) sequence, a degenerate primer (of at least about 17 residues) can be designed from nucleic acid encoding an amino acid sequence TC(glycine/Alanine)SHL (SEQ ID NO:52), encoded by a sequence such as 5'-AG(G/A)TGN(G/C)(T/A)N(G/C)C(G/A)CANGT-3') 3' (SEQ ID NO:53), Such a degenerate primer can be used to generate a binding domain incorporating TM I through TM VI, TM II through TM VI, TM III through TM VI or TM IV through TM VI).

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known olfactory receptor ligand binding regions (see, e.g., Rose (1998) Nucleic Acids Res. 26:1628–1635; Singh (1998) Biotechniques 24:318–319).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops (1997) Nucleic Acids Res. 25:4866–4871. Nonpolar molecules can also be used to mimic the shape of natural DNA bases. A non-hydrogen-bonding shape mimic for adenine can replicate efficiently and selectively against a nonpolar shape mimic for thymine (see, e.g., Morales (1998) Nat. Struct. Biol. 5:950–954). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill (1998) Proc. Natl. Acad. Sci. USA 95:4258–4263). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite ((the term "P" in the sequences, see above). This pyrimidine analog hydrogen bonds with purines, including A and G residues.

Exemplary primer pairs for amplification of olfactory receptor transmembrane domains II through VII include:

potential odorants and odorant effect on cell physiology, as described below). For example, cells can be identified by olfactory marker protein (OMP), an abundant cytoplasmic protein expressed almost exclusively in mature olfactory sensory neurons (see, e.g., Buiakova (1996) Proc. Natl. Acad. Sci. USA 93:9858–9863). Shirley (1983) Eur. J. Biochem. 32:485–494, describes a rat olfactory preparation suitable for biochemical studies in vitro on olfactory mechanisms. Cultures of adult rat olfactory receptor neurons are described by Vargas (1999) Chem. Senses 24:211–216. Because these cultured neurons exhibit typical voltage-gated currents and are responsive to application of odorants, they can also be used to express the hybrid olfactory receptors of the invention for odorant screening (endogenous olfactory receptor can be initially blocked, if desired, by, e.g., antisense, knockout, and the like). U.S. Pat. No. 5,869,266 describes culturing human olfactory neurons for neurotoxicity tests and screening. Murrell (1999) J. Neurosci. 19:8260–8270 describes differentiated olfactory receptor-expressing cells in culture that respond to odorants, as measured by an influx of calcium.

Genetic Engineering of Hybrid Receptor-encoding Sequences

The invention provides hybrid protein-coding sequences comprising polypeptide-encoding nucleic acids fused to the translocation sequences of the invention. Also provided are hybrid olfactory receptors comprising the translocation motifs and odorant/ligand-binding domains of olfactory receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, transgenics, of the invention, a promoter fragment can be employed to direct expression of the desired nucleic acid in all tissues.

```
(a) 5'-GGGGTCCGGAG(A/G)(C/G)(A/G)TA(A/G/T)AT(A/G/P)A(A/G/P)(A/G/P)GG-3'     (SEQ ID NO:1)
    and 5'-GGGGCTGCAGACACC(A/C/G/T)ATGTA(C/T)(C/T)T(A/C/G/T)TT(C/T)(C/T)T-3'.   (SEQ ID NO:2)

(b) 5'-GGGGTCCGGAG(A/G)(C/G)T(A/G)A(A/G/T)AT(A/G/P)A(A/G/P)(A/G/P)GG-3'     (SEQ ID NO:7)
    and 5'-GGGGCTGCAGACACC(A/C/G/T)ATGTA(C/T)(C/T)T(A/C/G/T)TT(C/T)(C/T)T-3'    (SEQ ID NO:8)

(c) 5'-GGGGTCCGGAG(A/G)(C/G)T(A/G)A(A/G/T)AT(A/G/C/T)A(A/G/C/T)             (SEQ ID NO:9)
    (A/G/C/T)GG-3' and 5'-GGGGCTGCAGACACC(A/C/G/T)ATGTA(C/T)(C/T)T(A/C/G/T)TT(C/T)(C/T)T-3'.   (SEQ ID NO:10).
```

Generating Nucleic Acids from Olfactory Receptor-Expressing Cells

The invention provides method for generating nucleic acids that encode ligand-binding regions of olfactory receptors by amplification (e.g., PCR) of appropriate nucleic acid sequences using degenerate primer pairs. The amplified nucleic acid can be genomic DNA from any cell or tissue or mRNA or cDNA derived from olfactory receptor-expressing cells, e.g., olfactory neurons or olfactory epithelium.

Isolation of from olfactory receptor-expressing cells is well known in the art (cells expressing naturally or inducibly expressing olfactory receptors can be used to express the hybrid olfactory receptors of the invention to screen for Olfactory cell-specific transcriptional elements can also be used to express the fusion polypeptide receptor of the invention, including, e.g., a 6.7 kb region upstream of the M4 olfactory receptor coding region. This region was sufficient to direct expression in olfactory epithelium with wild type zonal restriction and distributed neuronal expression for endogenous olfactory receptors (Qasba (1998) J. Neurosci. 18:227–236). Receptor genes are normally expressed in a small subset of neurons throughout a zonally restricted region of the sensory epithelium. The transcriptional or translational control elements can be isolated from natural sources, obtained from such sources as ATCC or GenBank libraries, or prepared by synthetic or recombinant methods.

The invention provides fusion proteins comprising the translocation motif of the invention. However, these fusion proteins can also comprise additional element for, e.g., protein detection, purification, or other applications. Detection and purification facilitating domains include, e.g., metal chelating peptides such as polyhistidine tracts or histidine-tryptophan modules or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi (1998) Biochimie 80:289–293), subtilisin protease recognition motif (see, e.g., Polyak (1997) Protein Eng. 10:615–619); enterokinase (Invitrogen, San Diego Calif.), and the like, between a translocation domain of the invention (for efficient plasma membrane expression) and the rest of the newly translated polypeptide may be useful to facilitate purification. For example, one construct can include a polypeptide-encoding nucleic acid sequence linked to six histidine residues followed by a thioredoxin, an enterokinase cleavage site (see, e.g., Williams (1995) Biochemistry 34:1787–1797), and an amino terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see e.g., Kroll (1993) DNA Cell. Biol., 12:441–53.

Cloning and Construction of Expression Vectors

The invention provides libraries of expression vectors comprising the olfactory binding domain-encoding sequences of the invention. These nucleic acids may be introduced into a genome or into the cytoplasm or a nucleus of a cell and expressed by a variety of conventional techniques, well described in the scientific and patent literature. See, e.g., Roberts (1987) Nature 328:731; Berger (1987) supra; Schneider (1995) Protein Expr. Purif. 6435:10; Sambrook, Tijssen or Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault (1997) Gene 190:315–317; Aubrecht (1997) J. Pharmacol. Exp. Ther. 281:992–997). Because selectable marker genes conferring resistance to substrates like neomycin or hygromycin can only be utilized in tissue culture, chemoresistance genes are also used as selectable markers in vitro and in vivo.

Structure of Seven-Transmembrane Receptors

The invention provides a chimeric nucleic acid sequence encoding an odorant/ligand binding domain within any 7-transmembrane polypeptide. 7-transmembrane receptors belong to a superfamily of transmembrane (TM) proteins having seven domains that transverse a plasma membrane seven times. Each of the seven domains spans the plasma membrane (TM I to TM VII). Because 7-transmembrane receptor polypeptides have similar primary sequences and secondary and tertiary structures, structural domains (e.g., TM domains) can be readily identified by sequence analysis. For example, homology modeling, Fourier analysis and helical periodicity detection can identify and characterize the seven domains within a 7-transmembrane receptor sequence. Fast Fourier Transform (FFT) algorithms can be used to assess the dominant periods that characterize profiles of the hydrophobicity and variability of analyzed sequences. To predict TM domains and their boundaries and topology, a "neural network algorithm" by "PHD server" can be used, as done by Pilpel (1999) Protein Science 8:969–977; Rost (1995) Protein Sci. 4:521–533. Periodicity detection enhancement and alpha helical periodicity index can be done as by, e.g., Donnelly (1993) Protein Sci. 2:55–70. Other alignment and modeling algorithms are well known in the art, see, e.g., Peitsch (1996) Receptors Channels 4:161–164; Cronet (1993) Protein Eng. 6:59–64 (homology and "discover modeling"); http://bioinfo.weizmann.ac.il/.

Olfactory Gene and Receptors

The library sequences of the invention include receptor sequences that correspond to TM ligand-binding domains, including, e.g., TM II to VII, TM II to VI, TM III to VII, and TM III to VII, that have been amplified (e.g., PCR) from mRNA of or cDNA derived from, e.g., olfactory receptor-expressing neurons or genomic DNA. Olfactory (or "odorant") receptors belong to the 7-transmembrane receptor superfamily; however they are also recognized as a distinct family of receptors. Olfactory receptors are G-protein-coupled receptors (Raming (1993) Nature 361:353–356). Genes encoding the olfactory receptors are active primarily in olfactory neurons (Axel (1995) Sci. Amer. 273:154–159). Individual olfactory receptor types are expressed in subsets of cells distributed in distinct zones of the olfactory epithelium (Breer (1994) Semin. Cell Biol. 5:25–32). The human genome contains thousands of genes that encode a diverse repertoire of olfactory receptors (Rouquier (1998) Nat. Genet. 18:243–250; Trask (1998) Hum. Mol. Genet. 7:2007–2020).

Identifying Olfactory Receptor TM Domain Structures and Sequences

The invention provides libraries of olfactory receptor odorant/ligand-binding TM domain sequences. These sequence can include a various TM domains or variations thereof, as describe above. These sequences can be derived from any 7-transmembrane receptor. Because these polypeptides have similar primary sequences and secondary and tertiary structures, the seven domains can be identified by various analyses well known in the art, including, e.g., homology modeling, Fourier analysis and helical periodicity (see, e.g., Pilpel (1999) supra), as described above. Using this information sequences flanking the seven domains can be identified and used to designed degenerate primers for amplification of various combinations of TM regions and subsequences for use in the compositions and methods of the invention.

Measuring Changes in Physiologic Activity Due to Olfactory Receptor-Ligand Binding The invention provides methods and compositions for determining whether a test compound specifically binds to a mammalian olfactory receptor in vitro or in vivo. The invention also provides methods and compositions for determining whether a test compound is neurotoxic to an olfactory neuron expressing an olfactory transmembrane receptor polypeptide. Any aspect of cell physiology can be monitored to assess the effect of odorant/ligand binding to a chimeric olfactory receptor of the invention.

Olfactory receptors are normally located on the specialized cilia of olfactory neurons. These receptors bind odorants and initiate the transduction of chemical stimuli into electrical signals. This process can involve a G protein-coupled activation of an adenylyl cyclase, which leads to a rise in cAMP and consequently the opening of cyclic nucleotide-activated, non-selective cation channels. These open channels produce a cation influx that results in the depolarization of the olfactory neuron. Another olfactory transduction mechanism can also include the generation of $IP_3$ and the opening of $IP_3$-activated channels on the ciliary plasma membrane. Electro-olfactograms can measure the mass response of sensory neurons in the olfactory epithelium (discussed below).

Cell Culture Assays

The invention provides methods and compositions for expressing the chimeric olfactory receptors of the invention in cells to screen for odorants that can specifically bind and the effect (e.g., biochemical or electrophysiological) of such binding on cell physiology. Any cell expression system can be used, e.g., mammalian cell expression systems. Cells that normally express olfactory receptors can be used, particularly to study the physiological effect of an odorant on a cell. Isolation and/or culturing of such cells and their transformation with chimeric olfactory receptor-expressing sequences of the invention can be done with routine methods, as described above. See, e.g., description of cultured neurons that exhibit typical voltage-gated currents and are responsive to application of odorants. Vargas (1999) supra; olfactory neurons from rats (Coon (1989) Proc. Natl. Acad. Sci. USA 86:1703–1707). However, the neurotoxicity of various agents to humans could be more accurately determined using cultured human neurons than cultured non-human neurons.

To evaluate electrophysiologic effects of ligand binding to cell-expressed chimeric receptor, patch-clamping of individual cells can be done. Patch-clamp recordings of the olfactory receptor cell membrane can measure membrane conductances. Some conductances are gated by odorants in the cilia and depolarize the cell through cAMP- or IP3-sensitive channels, depending on the species. Other conductances are activated by membrane depolarization and/or an increased intracellular Ca2+ concentration. See, e.g., Trotier (1994) Semin. Cell Biol. 5:47–54.

Changes in calcium ion levels in the cell after exposure of the cell to known or potential odorant/ligands can be accomplished by a variety of means. For example, cells can be pre-loaded with reagents sensitive to calcium ion transients, e.g., Fura-2 (see, e.g., Rawson (1997) J. Neurophysiol. 77:1606–1613; Restrepo (1996) J. Neurobiol. 30:37–48). Measurement of calcium transients is described in detail in Example 1, below. For example, Kashiwayanagi (1996) Biochem. Biophys. Res. Commun. 225:666–671 measured both of inositol 1,4,5-trisphosphate induces inward currents and Ca2+ uptake in frog olfactory receptor cells.

Other physiologic mechanisms can also be measured, e.g., plasma membrane homeostasis parameters (including lipid second messengers), cellular pH changes (see, e.g., Silver (1998) Methods Cell Biol. 56:237–251), G proteins (see, e.g., Quartara (1997) Neuropeptides 31:537–563); cAMP, and the like.

Non-human Animal Assays

The invention also provides non-human animals expressing one or more hybrid olfactory receptor sequences of the invention, particularly human olfactory receptor sequences. Such expression can be used to determine whether a test compound specifically binds to a mammalian olfactory transmembrane receptor polypeptide in vivo by contacting a non-human animal stably or transiently infected with a nucleic acid derived from the library of the invention with a test compound and determining whether the animal reacts to the test compound by specifically binding to the receptor polypeptide.

Use of the translocation domains of the invention in the fusion polypeptides generates a cell expressing high levels of olfactory receptor. Animals infected with the vectors of the invention are particularly useful for assays to identify and characterize odorants/ligands that can bind to a specific or sets of receptors. Such vector-infected animals expressing libraries of human olfactory sequences can be used for in vivo screening of odorants and their effect on, e.g., cell physiology (e.g., on olfactory neurons), on the CNS (e.g., olfactory bulb activity), or behavior.

Means to infect/express the libraries of nucleic acids and vectors of the invention are well known in the art, as described above. A variety of individual cell, organ or whole animal parameters can be measured by a variety of means. For example, recording of stimulant-induced waves (bulbar responses) from the main olfactory bulb or accessory olfactory bulb is a useful tool for measuring quantitative stable olfactory responses. When electrodes are located on the olfactory bulb surface it is possible to record stable responses over a period of several days (see, e.g., Kashiwayanagi (1997) Brain Res. Brain Res. Protoc. 1:287–291). In this study, electroolfactogram recordings were made with a four-electrode assembly from the olfactory epithelium overlying the endoturbinate bones facing the nasal septum. Four electrodes were fixed along the dorsal-to-ventral axis of one turbinate bone or were placed in corresponding positions on four turbinate bones and moved together up toward the top of the bone. See also, Scott (1997) J. Neurophysiol. 77:1950–1962; Scott (1996) J. Neurophysiol. 75:2036–2049; Ezeh (1995) J. Neurophysiol. 73:2207–2220. In other systems, fluorescence changes in nasal epithelium can be measured using the dye di-4-ANEPPS, which is applied on the rat's nasal septum and medial surface of the turbinates (see, e.g., Youngentob (1995) J. Neurophysiol. 73:387–398). Extracellular potassium activity (aK) measurements can also be carried out in in vivo. An increase in aK can be measured in the mucus and the proximal part of the nasal epithelium (see, e.g., Khayari (1991) Brain Res. 539:1–5).

The chimeric olfactory receptor of the invention can be expressed in animal nasal epithelium by delivery with an infecting agent, e.g., adenovirus expression vector. Recombinant adenovirus-mediated expression of a recombinant gene in olfactory epithelium using green fluorescent protein as a marker is described by, e.g., Touhara (1999) Proc. Natl. Acad. Sci. USA 96:4040–4045.

Transgenic Non-human Animals Incorporating Hybrid Olfactory Receptors

The invention also provides non-human animals genetically engineered to express one or more hybrid olfactory receptor sequences of the invention, particularly human olfactory receptor sequences. Because the translocation domains of the invention in the fusion polypeptides generates an animal expressing high levels of olfactory receptor, these animals and their progeny are particularly useful for assays to identify and characterize odorants/ligands that can bind to a specific or sets of receptors.

The endogenous olfactory receptor genes can remain functional and wild-type (native) activity can still be present. In other situations, where it is desirable that all olfactory receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu (1997) Transgenic Res 6: 97–106). The insertion of the exogenous sequence is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet (1998) Hum. Mol. Genet. 7:53–62; Moreadith (1997) J. Mol. Med. 75:208–216; Tojo (1995) Cytotechnology 19:161–165; Mudgett (1995) Methods Mol. Biol. 48:167–184; Longo (1997) Transgenic Res. 6:321–328; U.S. Pat. Nos. 5,616,491; 5,464,764; 5,631,153; 5,487,992; 5,627,059; 5,272,071; and, WO 91/09955, WO 93/09222, WO 96/29411, WO 95/31560, and WO 91/12650.

The nucleic acid libraries of the invention can also be used as reagents to produce "knockout" human cells and their progeny.

Kits

The invention provides kits that contain degenerate primer pairs of the invention. cDNA libraries from olfactory epithelium can also be included. The kits can contain recombinant adenoviruses comprising a single construct or libraries of expression vectors of the invention. The kit can also contain replication-competent cells, such as 293 cells. The kit can contain instructional material teaching methodologies, e.g., means to amplify nucleic acid, infect animals, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Identification of Odorant/Ligands for Olfactory Receptors with Binding Sites Generated by PCR Amplification with Degenerate Primers by Functional Expression of Libraries of the Receptors in Human Cell Lines The following example sets forth the generation of an expression plasmid library containing a large and diverse repertoire of nucleic acids encoding odorant/ligand binding regions comprising transmembrane (TM) II–VII regions of mouse olfactory receptor sequences. From this library, 80 chimeric receptors were tested against 26 odorants after transient transfection into the human cell line HEK-293. Three receptors were identified that responded to micromolar concentrations of carvone, (–) citronellal and limonene, respectively.

A PCR-based amplification strategy taking advantage of the homology shared among olfactory receptors at the beginning of TM II and the end of TM VII was used to generate a library containing a large number of olfactory-receptor sequences. The structure of the overall construct, pCMV-Rho/M4$_{NC}$, is shown in FIG. 1A. The degenerate oligonucleotides are flanked by the coding sequences for the appropriate regions of the mouse M4 olfactory receptor (described by, e.g., Qasba (1998) J. Neurosci. 18:227–236).

Making a Chimeric Receptor Cassette and Vector for Eukaryotic Expression

Chimeric receptor expression vectors were assembled from a pBK-CMV plasmid (Stratagene, San Diego, Calif.) modified such that the lac Z sequences between nucleotides 1098 and 1300 were deleted. A PCR fragment consisting of 45 nucleotides upstream of the bovine rhodopsin initiation codon and the first 60 nucleotides of the coding region (designated "rho-tag" in FIG. 1A) was introduced between the BamHI and EcoRI sites. Restriction fragments corresponding to the first 57 amino acids (the N-terminus to TM II, EcoRI/PstI restriction sites) (SEQ ID NO:1) and to the last 22 amino acids (BspEI/XbaI restriction sites) (SEQ ID NO:2) of the mouse M4 olfactory receptor were cloned into the rhodopsin-tag ("rho-tag") vector. The resulting vector (designated pCMV-Rho/M4$_{NC}$) possesses unique PstI and BspEI sites at the beginning of TM II and the end of TM VII, respectively (see FIG. 1A).

PCR Amplification

The mouse olfactory-receptor transmembrane II–VII library was amplified using PCR. The PCR reaction mixture contained: Taq and Pfu polymerase (Stratagene, San Diego, Calif.) 0.5 U each, 0.2 mM dNTP, 1 µM of each primer (degenerate oligonucleotides SEQ ID NO:1 and SEQ ID NO:2) and either 100 ng mouse genomic DNA ($\beta_2$-adrenergic receptor sequence), 10 ng plasmid template DNA, or 50 to 100 ng 1$^{st}$ strand cDNA template prepared from mouse C57BL/6J olfactory epithelium. One amplification protocol was one cycle of 2 min at 94° C.; 30 cycles at (55° C., 72° C., 94° C.), 1 min each; 1 cycle at (55° C., 72° C.), 10 min. A second amplification protocol was 1 cycle for 2 min at 94° C.; 34 cycles at (45° C., 72° C., 94° C.), 1 min each; and 1 cycle at (45° C., 72° C.), 10 min. The second procotol, having a lower hybridization temperature (45° C. versus 55°

C.) generated an equally diverse library of binding domains. A library of PCR products of about 0.7 kilobase was generated.

Analysis of Amplified Odorant/Ligand-binding Sequence Library

Sequencing and sequence identity analysis of 26 randomly chosen PCR amplification products was performed. Deduced amino acid sequences were aligned by the ClustalW algorithm using default values established by DNAstar alignment software (DNASTAR, Inc., Madison, Wis.) (see, e.g., Burland (2000) Methods Mol. Biol. 132:71–91).

This analysis revealed that all but three of the sequenced odorant/ligand binding region inserts were distinct polypeptide-coding receptor sequences. Exemplary odorant/ligand binding region nucleic acid sequences generated by amplification of *Mus musculus* cDNA, and the respective deduced amino acid sequences, include (a) (SEQ ID NO:11)
```
  1 agtgtcttat ccattctgga tatgggctat gtcaccacca cagtgcccca gatgctggta
 61 catctggtct gtaagaagaa gaccatatcc tatgttggat gtgtggctca gatgtacatc
121 ttcctgatgc tgggaatcac cgagtcttgg ctgtttgcaa tcatggccta tgataggtat
181 gtggccattt gccatcccct cagatacaaa gtcatcatga gtcctttgct gcgcgggtca
241 ctggtagcct tctgtgggtt ctggggtatc acctgtgccc tgatatatac tgtttctgct
301 atgattcttc cctactgtgg ccccaatgag atcaaccact tcttctgtga agtgcctgct
361 gtcctgaagc tggcctgcgc agacacctct cccaatgacc aggtagactt catcctaggc
421 tttatccttc ttttggtccc actctccctc atcattgttg tctacatcaa tatctttgct
481 gctatcttga aatccgttc aactcaaggg aggatcaagg ccttctccac ctgtgtgtcc
541 cacatcactg tggtcaccat gttctccatc ccgtgtatgg ttatgtatat gaggcctggc
601 tctgagtcct ccccagaaga ggacaagaag ttggctctgt tctacaacgt catctctgcc
661 ttcctcaac
``` with a deduced amino acid sequence (SEQ ID NO:12)
```
SVLSILDMGYVTTTVPQMLVHLVCKKKTISYVGCVAQMYIFLML
GITESWLFAIMAYDRYVAICHPLRYKVIMSPLLRGSLVAFCGFWGITCALIYTVSAMI
LPYCGPNEINHFFCEVPAVLKLACADTSPNDQVDFILGFILLLVPLSLIIVVYINIFA
AILRIRSTQGRIKAFSTCVSHITVVTMFSIPCMVMYMRPGSESSPEEDKKLALFYNVI
SAFLN
```

(b) (SEQ ID NO:13)
```
  1 tgcaacctgg ccaccatgga cattgtgtgc accccctctg tgattcctaa ggccctgatt
 61 ggcctagtgt ctgaagaaaa caccatctcc ttcaaaggat gcatggctca gctcttcttt
121 cttctgtggt ccttgtcttc ggagctgctg ctgctcacgg tcatggccta tgaccgctat
181 gtggccatct gctttcccct gcactacagc tctagaatga gcccacagct ctgtggggcc
241 ctggccgtgg gtgtatggtc catctgtgct gtgaatgcat ctgtgcacac tggcctgatg
301 acacggctgt cattctgtgg ccccaaggtc atcacccact tcttctgtga gattccccca
361 ctcctcctgc tttcctgtag tcccacatac attaatagcg ttatgacact tgtggcagat
421 gccttttatg ggtgcatcaa ctttgtgcta accttgttat cctatggctg catcattgcc
481 agtgttctgc gcatgcgttc tgctgagggc aagaggaagg ccttttctac ctgttcatcc
541 cacctcatcg tggtctcagt gtactactca tctgtgttct gtgcctatgt cagtcctgcc
601 tccagctaca gcccagaaag aagcaaagtt acctccgtgc tgtactcgat cctcagccca
661 accctgaac
``` with a deduced amino acid sequence (SEQ ID NO:14)
CNLATMDIVCTPSVIPKALIGLVSEENTISFKGCMAQLFFLLWS
LSSELLLLTVMAYDRYVAICFPLHYSSRMSPQLCGALAVGVWSICAVNASVHTGLMTR
LSFCGPKVITHFFGEIPPLLLLSCSPTYINSVMTLVADAFYGCINFVLTLLSYGCIIA
SVLRMRSAEGKRKAFSTCSSHLIVVSVYYSSVFCAYVSPASSYSPERSKVTSVLYSIL
SPTLN (c) (SEQ ID NO:15)
```
  1 tgcaacctgg ccaccatgga tattatctgc acctcctctg tgctgcccaa ggcgctggtt
 61 ggtctactat ctgaggaaaa caccatctcc tttaaagggt gcatggccca gctcttcttc
121 cttgtgtggt ccttgtcttc agagctgctg ctgctcacag tcatggccta tgaccgctat
181 gtggccatct gctttcccct gcactacagc tctagaatga gcccacagtt gtgtgggct
241 ctggccatgg gtgtatggtc catctgtgct ctgaatgcat ctatcaacac tggtctgatg
301 acacggctgt cattctgtgg acccaaggtc atcacccact tcttctgtga gattccccca
361 ctccttctgc tctcctgtag ccccacatac gtaaacagca ttatgactct aatagcagat
421 gtcttctatg gaggcatcaa ttttgtgctt accttactat cctatggctg catcattgcc
481 agcatcctgc gcatgcgttc tgctgagggc aagaggaagg ccttttctac ctgctcatcc
541 cacctcatcg tggtctctgt gtactactca tctgtgttct gtgcctatgt cagccctgca
601 tccagctata gcccagaaag aagcaaagtt acctctgtgt tgtactcatt cctcagccca
661 accctgaac
``` with a deduced amino acid sequence (SEQ ID NO:16)
CNLATMDIICTSSVLPKALVGLLSEENTTISFKGCMAQLFFLVWS
LSSELLLLTVMAYDRYVAICFPLHYSSRMSPQLCGALAMGVWSICALNASINTGLMTR
LSFCGPKVITHFFCEIPPLLLLSCSPTYVNSIMTLIADVFYGGINFVLTLLSYGCIIA
SILRMRSAEGKRKAFSTCSSHLIVVSVYYSSVFCAYVSPASSYSPERSKVTSVLYSFL
SPTLN (d) (SEQ ID NO:17)
```
  1 gccaccctt cctgtgttga catcctcttc acctccacca cagtgcccaa ggccctagtg
 61 aacatccaca cccaaagcag gacaatctcc tatgcaggat gcctggtcca gctctatttt
121 ttcctgactt tggagacat ggacatcttt ctcctggcca caatggccta tgaccgcttt
181 gtagctattt gtcaccctct ccactatagg atgatcatga gcttccagcg ctgctcactc
241 ttagtgacag tctgttggac ccttacaacc gttgtggcca tgacacacac cttcctcata
301 ttccggctct ccttctgctc tcagaaggtc attccagact tcttctgtga cctgggaccc
361 ctaatgaaga tcgcttgctc tgaaacccgg atcaatgagc ttgtgcttct cttcctgggg
421 ggtgcagtca tcttaatccc cttttttgctc atccttatgt cttatatccg cattgtttca
481 gccatcctca gggtcccttc tgcccaagga aggcgtaagg ccttttctac ctgtgggtcc
541 cacctttctg tggtggccct attctttggg actgtgataa gggcttatct atgtccttca
601 tcctcttcct ctaactcagt ggtagaggac acagcagcag ctgtcatgta tacagtggtg
661 actcccgtgc tgaac
``` with a deduced amino acid sequence (SEQ ID NO:18)
ATLSCVDILFTSTTVPKALVNIHTQSRTISYAGCLVQLYFFLTF
GDMDIFLLATMAYDRFVAICHPLHYRMIMSFQRCSLLVTVCWTLTTVVAMTHTFLIFR
LSECSQKVIPDFFCDLGPLMKIACSETRINELVLLFLGGAVILIPFLLILMSYIRIVS
AILRVPSAQGRRKAFSTCGSHLSVVALFFGTVIRAYLCPSSSSSNSVVEDTAAAVMYT
VVTPVLN (e) (SEQ ID NO:19)
```
  1 agtcagctct ccctcatgga cctcatgctg gtctgtaaca ttgtgccaaa gatggcagtc
 61 aacttcctgt ctggcaggaa gtccatctct tttgccggct gtggcataca aatcggattt
121 tttgtctctc ttgtgggatc agagggtctc ttgttaggac tcatggctta tgatcgctat
181 gtggccatta gccacccact tcactatccc attctcatga ccaaaaggt ctgtctccag
241 attgctggaa gttcctgggc ttttgggatc cttgatggaa taattcagat ggtggcagcc
301 atgagcctgc cctactgtgg ctcacggtat atagatcact tcttctgtga agtgccggct
361 ttactgaagc tggcctgtgc agacacctcc cttttcgaca ccctgctctt tgcttgctgt
421 gtctttatgc tgcttcttcc tttctcgatc attgtgactt cctatgctcg catcttgggg
481 gctgtgctcc gtatgcactc tgcccagtcc cgaaaaaagg ccctggccac ttgttcctcc
541 cacctgacag ctgtctctct cttctacggg gcagcaatgt tcatctacct gaggccaagg
601 cgatatcgcg ctcctagcca tgacaaagtt gtctcaatct tctacacagt tcttactcct
661 atgctcaac
``` with a deduced amino acid sequence (SEQ ID NO:20)
SQLSLMDLMLVCNIVPKMAVNFLSGRKSISFAGCGIQIGFFVSL
VGSEGLLLGLMAYDRYVAISHPLHYPILMSQKVCLQIAGSSWAFGILDGIIQMVAAMS
LPYCGSRYIDHFFCEVPALLKLACADTSLFDTLLFACCVFMLLLPFSIIVTSYARILG
AVLRMHSAQSRKKALATCSSHLTAVSLFYGAAMFIYLRPRRYRAPSHDKVVSIFYTVL
TPMLN (f) (SEQ ID NO:21)
```
  1 tacaaccttt cattgtctga catgggcttt agcagcacca caatcccaa atgctgata
 61 aacttgcatg cacataagag atccacaaca tatgctgaat gcctaactca ggtatctttc
121 tttattcttt ttgggtgtat ggacagcttt ctactggcag tgatggcata tgaccgatgg
181 gtggccattt gtcaccctct acactaccaa gtcattctga atccttgtcg gtgtagatat
241 ttggttgtaa tgtcattttg tatcagtctc attgattcac aggtgcactg ctttatggtg
301 tcacaactaa catttgtac taatatagaa atccctcatt tcttctgtga tgttccagaa
361 cttgtaaaac ttgcttgttc taacactact atcaatgaca tagccatgtt tctttcaagc
421 atcattgttg gattcctccc tgcctcagga atatttact cctactataa aattacttct
481 tctattttta gagttccatc actgttaggg aaatataaag ccttctctac ctgtggatct
541 cacctgtcag ttgtttgcct attttatgga acaggtatag gagtttacct cagttccaca
601 gtttctggtt cttccaggga aagtatggta gcttcggtaa tgtatacaat ggtggttcct
661 atgatgaac
``` with a deduced amino acid sequence (SEQ ID NO:22)
YNLSLSDMGFSSTTIPKMLINLHAHKRSTTYAECLTQVSFFILF

GCMDSFLLAVMAYDRWVAICHPLHYQVILNPCRCRYLVVMSFCISLIDSQVHCFMVSQ

LTFCTNIEIPHFFCDVPELVKLACSNTTINDIAMFLSSIIVGFLPASGIFYSYYKITS

SIFRVPSLLGKYKAFSTCGSHLSVVCLFYGTGIGVYLSSTVSGSSRESMVASVMYTMV

VPMMN (g) (SEQ ID NO:23)
```
  1 agtcagctct ccctcatgga cctcatgctg gtctgtaaca ttgtgccaaa gatggcagtc
 61 aacttcctgt ctggcaggaa gtccatctct tttgccggct gtggcataca aatcggattt
121 tttgtctctc ttgtgggatc agagggtctc ttgttaggac tcatggctta tgatcgctat
181 gtggccatta gccacccact tcactatccc attctcatga ccaaaaggt ctgtctccag
241 attgctggaa gttcctgggc ttttgggatc cttgatggaa taattcagat ggtggcagcc
301 atgagcctgc cctactgtgg ctcacggtat atagatcact tcttctgtga agtgccggct
361 ttactgaagc tggcctgtgc agacacctcc cttttcgaca ccctgctctt tgcttgctgt
421 gtctttatgc tgcttcttcc tttctcgatc attgtgactt cctatgctcg catcttgggg
481 actgtgctcc gtatgcactc tgcccagtcc cgaaaaaagg ccctggccac ttgttcctcc
541 cacctgacag ctgtctctct cttctacggg gcagcaatgt tcatctacct gaggccaagg
601 cgatatcgcg ctcctagcca tgacaaagtt gtctcaatct tctacacagt tcttactcct
661 atgctcaac
``` with a deduced amino acid sequence (SEQ ID NO:24)
SQLSLMDLMLVCNIVPKMAVNFLSGRKSISFAGCGIQIGFFVSL

VGSEGLLLGLMAYDRYVAISHPLHYPILMSQKVCLQIAGSSWAFGILDGIIQMVAAMS

LPYCGSRYIDHFFCEVPALLKLACADTSLFDTLLFACCVFMLLLPFSIIVTSYARILG

TVLRMHSAQSRKKALATCSSHLTAVSLFYGAAMFIYLRPRRYRAPSHDKVVSIFYTVL

TPMLN (h) (SEQ ID NO:25)
```
  1 tctaatctgt cctttgtgga catctgcttc acttccacca ctgttccaca gatgctggta
 61 aacattcaca cacaaagcaa ggccatcacc tatgcaggct gcatcatcca aatgtacttc
121 ttactgcttt tttcagggtt agacatcttt ctgctgactg tgatggccta tgaccgctat
181 gtggccatct gtcacccct gcattacatg atcatcatga gcacaagacg ctgtggattg
241 atgattctgg catgctggat tataggtgtt ataaattccc tgttacacac cttttttggtg
301 ttacggctgt cattctgcac aaacttggaa atccccatt ttttctgtga acttaatcaa
361 gttgtacacc aggcctgttc tgacaccttt cttaatgata tggtaattta cattacagct
421 atgctactgg ctgttggccc cttctctggt atcctttact cttactctag gatagtatcc
481 tccatttgtg caatcctcc agtgcagggg aagtacaaag catttccac ctgtgcatct
541 cacctctcag ttgtctcctt atttattgc accctcctgg gagtgtacct cagctctgct
601 gtgacccaaa actcacatgc tactgcaaca gcttcattga tgtacactgt ggtcaccccc
661 atgctgaac
``` with a deduced amino acid sequence (SEQ ID NO:26)
SNLSFVDICFTSTTVPQMLVNIHTQSKAITYAGCIIQMYFLLLF

SGLDIFLLTVMAYDRYVAICHPLHYMIIMSTRRCGLMILACWIIGVINSLLHTFLVLR

LSFCTNLEIPHFFCELNQVVHQACSDTFLNDMVIYITAMLLAVGPFSGILYSYSRIVS

SICAISSVQGKYKAFSTCASHLSVVSLFYCTLLGVYLSSAVTQNSHATATASLMYTVV

TPMLN (i)                                                          (SEQ ID NO:27)
  1 agtcagctct ccctcatgga cctcatgctg gtctgtaaca ttgtgccaaa gatggcagtc
 61 aacttcctgt ctggcaggaa gtccatctct tttgccggct gtggcataca aatcggattt
121 tttgtctctc ttgtgggatc agagggtctc ttgttaggac tcatggctta tgatcgctat
181 gtggccatta gccacccact tcactatccc attctcatga ccaaaaggt ctgtctccag
241 attgctggaa gttcctgggc ttttgggatc cttgatggaa taattcagat ggtggcagcc
301 atgagcctgc cctactgtgg ctcacggtat atagatcact tcttctgtga agtgccggct
361 ttactgaagc tggcctgtgc agacacctcc cttttcgaca ccctgctctt tgcttgctgt
421 gtctttatgc tgcttcttcc tttctcgatc attgtgactt cctatgctcg catcttgggg
481 gctgtgctcc gtatgcactc tgcccagtcc cgaaaaaagg ccctggccac ttgttcctcc
541 cacctgacag ctgtctctct cttctacggg gcagcaatgt tcatctacct gaggccaagg
601 cgatatcgcg ctcctagcca tgacaaagtt gtctcaatct tctacacagt tcttactcct
661 atgctcaac with a deduced amino acid sequence (SEQ ID NO:28)
SQLSLMDLMLVCNIVPKMAVNFLSGRKSISFAGCGIQIGFFVSL

VGSEGLLLGLMAYDRYVAISHPLHYPILMSQKVCLQIAGSSWAFGILDGIIQMVAAMS

LPYCGSRYIDHFFCEVPALLKLACADTSLFDTLLFACCVFMLLLPFSIIVTSYARILG

AVLRMHSAQSRKKALATCSSHLTAVSLFYGAAMFIYLRPRRYRAPSHDKVVSIFYTVL

TPMLN (j)                                                          (SEQ ID NO:29)
  1 tgtgccctct ccatctctga gattttctac acctttgcca tcatcccacg catgttggct
 61 gacctgctca ccacacttca ctccatcgcc tttctggcct gtgccagcca gatgttcttc
121 tccttcacat ttggcttcac ccattccttt ctactcaccg tcatgggcta tgaccgctac
181 gtggccatct gtcacccact gagatacaat gtgctcatga gccccgtgg ctgtgcctgc
241 ctggtagcct ggtcctgggt tggtggatca ttcatgggga cagtggtgac gacagccatt
301 ttcaacctca cattctgtgg acccaatgag atccaccatt ttacttgtca tgttccacct
361 ctattgaagt tggcatgcgg agagaatgta ctggaggtgg caagggtgt agaaatagtg
421 tgcatcacag ccctcctggg ctgctttctc ctcatcctcc tctcatatgc cttcattgtg
481 gttaccatct tgaagatacc atcagctgag ggtcggcaca aggctttctc cacatgtgca
541 tcccacctca cagtggtggt tgtacattat ggctttgctt ctgtcattta cctcaagcct
601 aagggcccca gtctctggaa ggagatact ctgatgggca tcacctacac agtcctcacc
661 cccttcctta gt atgctcaac with a deduced amino acid sequence

```
                                                              (SEQ ID NO:30)
    CALSISEIFYTFAIIPRMLADLLTTLHSIAFLACASQMFFSFTF

GFTHSFLLTVMGYDRYVAICHPLRYNVLMSPRGCACLVAWSVVGGSFMGTVVTTAIFN

LTFCGPNEIHHFTCHVPPLLKLACGENVLEVAKGVEIVCITALLGCFLLILLSYAFIV

VTILKIPSAEGRHKAFSTCASHLTVVVVHYGFASVIYLKPKGPKSLEGDTLMGITYTV

LTPFLS (k)                                                           (SEQ ID NO:31)
  1 tgcaacttag cgaccatgga tattatctgc acctcctctg tactgcccaa ggcgctggtt
 61 ggtctactgt ctgaggaaaa caccacctcc ttcaaagggt gcatgactca gctcttcttt
121 cttgtgtggt ctggatcctc tgagctgctg ctgctcacag tcatggccta tgaccgctat
181 gtggccatct gtttgcccct gcattacagc tctaggatga gtccacagct ctgtgggacc
241 tttgccgtgg gtgtatggtc catctgcgca ctaaatgcat ctatcaacac tggtctgatg
301 acacggctgt cattctgtgg ccccaaggtc atcaccact tcttctgtga gattcccca
361 ctcctcctgc tctcctgtag tcctacatat ataaatagcg ttatgactct tgtggcagat
421 gccttttatg gaggcatcaa ttttttactt accttgctat cctatggctg catcattgcc
481 agcatcctgc gcatgcgttc tgctgagggc aagaggaagg cctttctac ctgctcatcc
541 cacctcattg tggtctctgt gtactactca tctgtgttct gtgcctatgt cagccctgct
601 tctagctaca gcccagaaag aagcaaagtt tcctcagtgc tgtactcagt cctcagccca
661 accctcaac
``` with a deduced amino acid sequence

```
                                                              (SEQ ID NO:32)
    CNLATMDIICTSSVLPKALVGLLSEENTTSFKGCMTQLFFLVWS

GSSELLLLTVMAYDRYVAICLPLHYSSRMSPQLCGTFAVGVWSICALNASINTGLMTR

LSFCGPKVITHFFCEIPPLLLLSCSPTYINSVMTLVADAFYGGINFLLTLLSYGCIIA

SILRMRSAEGKRKAFSTCSSHLIVVSVYYSSVFCAYVSPASSYSPERSKVSSVLYSVL

SPTLN (l)                                                           (SEQ ID NO:33)
  1 gccaaccttt ccttcgttga tgtctgcttc accaccaatc tcatccccag gctcctggct
 61 ggccatgtgg ctggaacaag gaccatctct tatgtccact gcctaactca gacgtacttc
121 ctgatttctt ttgccaatgt ggacaccttt ctgctggctg ccatgcgccct ggacagattt
181 gtggccatat gctacccact acagtaccac accatcatca ccccccagct ctgtgtgggg
241 ctggcagccg ttgtgtggat gtgctctgcc ctcatctctc tgatgcacac actcctcatg
301 agcagactga gtttctgctc ctccatcccg gagatctctc acttctactg tgatgcttac
361 ctgctcatga agttggcctg ttcagacaca cgagtcaatc aacttgtctt cctgggagct
421 gtggtcctct ttgtggcccc ctgcattctc attgtggtct cttatgtccg aatcaccatg
481 gtggtcctcc agatcccctc tgcaaagggc cggcacaaga catttccac atgtagctca
541 cacttgtctg tggtcactct gttctatggc acagtactgg gtatctatat acgacctcca
601 gactccttct ccacccagga cacggtagcc accatcatgt atactgtggt taccccccatg
661 ctgaac
``` with a deduced amino acid sequence (SEQ ID NO:34)
ANLSFVDVCFTTNLIPRLLAGHVAGTRTISYVHCLTQTYFLISF

ANVDTFLLAAMALDRFVAICYPLQYHTIITPQLCVGLAAVVWMCSALISLMHTLLMSR

LSFCSSIPEISHFYCDAYLLMKLACSDTRVNQLVFLGAVVLFVAPCILIVVSYVRITM

VVLQIPSAKGRHKTFSTCSSHLSVVTLFYGTVLGIYIRPPDSFSTQDTVATIMYTVVT

PMLN (m) (SEQ ID NO:35)
```
  1 tgcaacctgg ctaccacgga tattgtgtgc acctcctctg tgattcctaa ggccctgatt
 61 ggcctagtat ctgaggaaaa catcatcacc ttcaagggat gtatggccca gctcttcttc
121 cttgcatggg caacatccgc agagctgttg ctgctcacgg tcatggccta tgaccgctat
181 gtggctatct gctttcccct acactacagc tctaggatga gcccacagct ctgtggagca
241 ctggccgtgg gtgtatggtc catcagtgct gtgaatgcat ctgtgcacac tggcctgatg
301 acacggctgt cattctgtgg acccaaggtc atcacccact tcttctgtga gaccccca
361 ctcctcctgc tctcctgtag ttccacatac attaatagtg ttatgacact tgtggcagat
421 gtctttctgg gaggcatcaa cttcatgtta accctgttat cttatggctt catcattgcc
481 agcatcctgc gcatgcgttc tgctgagggc aagaggaagg ccttttctac ctgctcatcc
541 cacctcatcg tggtttctgt gtactactca tctctgttct gtgcctatat cagccctgct
601 tctagctaca gcccagaaag aagcaaagtt tcctcagtgc tgtactcagt cctcagccca
661 accctcaac
``` with a deduced amino acid sequence (SEQ ID NO:36)
CNLATTDIVCTSSVIPKALIGLVSEENIITFKGCMAQLFFLAWA

TSAELLLLTVMAYDRYVAICFPLHYSSRMSPQLCGALAVGVWSISAVNASVHTGLMTR

LSFCGPKVTTHFFCEIPPLLLLSCSSTYINSVMTLVADVFLGGINFMLTLLSYGFIIA

SILRNRSAEGKRKAFSTCSSHLIVVSVYYSSLFCAYISPASSYSPERSKVSSVLYSVL

SPTLN (n) (SEQ ID NO:37)
```
  1 agcaacctgg cttttgttga tttctgctac tcctctgtca ttacacctaa gatgcttggg
 61 aatttcttgt atagcaaaaa tgccatatcc ttcaatgcat gtgctgccca gttaggctgc
121 tttctcacat ttatggtatc agagtgcttg ctcctggctt ccatggcata tgatagatat
181 gcagcaattt gtaaccctct attgtatatg gtcacaatgt ctcctggaat ctgcattcag
241 cttgtagttg tgccctatag ctatagtttc ctcatggcat tgattcacac tcttctaacc
301 ttccgcctat cctattgcca ttctaatatc atcaatcact tctactgtga tgacatgcct
361 cttctcaggc taacttgctc agatactcac tacaagcagc tgtctatttt ggcctgtgct
421 ggaatcacat tcatttcttc tgttctgatt gtttctgtat cctacatgtt cattatttct
481 gccattctga ggatgcgctc agctgaagga agacggaaag ccttttccac ctgtagctct
541 cacatgatgg cagtgagcat attctatgga actcttatct ttatgtactt acagccgagc
601 tctgaccatt ctcttgatac agataagatg gcctctgtct tctacacagt gatcatcccc
661 atgttgaac
``` with a deduced amino acid sequence (SEQ ID NO:38)
SNLAFVDFCYSSVITPKMLGNFLYSKNAISFNACAAQLGCFLTF

MVSECLLLASMAYDRYAAICNPLLYMVTMSPGICIQLVVVPYSYSFLMALIHTLLTFR

LSYCHSNIINHFYCDDMPLLRLTCSDTHYKQLSILACAGITFISSVLIVSVSYMFIIS

AILRMRSAEGRRKAFSTCSSHMMAVSIFYGTLIFMYLQPSSDHSLDTDKMASVFYTVI

IPMLN (o)                                                        (SEQ ID NO:39)
  1 agtcacttgt ccttcattga catgatgtac atctcaacca ttgtgcccaa aatgctagtt
 61 gattatcttc tagggcaaag gactatttcc tttgtgggat gcacagctca cactttcta
121 tacctcaccc tggtgggagc cgagttcttt cttctgggcc tcatggctta tgatcgttat
181 gtggccatct gcaacccact gaggtaccct gtcctcatga gccgccggat ctgttggatt
241 atcatagcag gctcctggtt tgggggatct ttggatggct tcctcctcac tccaatcacc
301 atgagttttc ctttctgtag atcacgagag attaaccact tcttctgtga ggcacctgct
361 gtgctgaagt tggcatgtgc agacacagcc ctctatgaga cggtgatgta tgtgtgctgc
421 gttctgatgc tgttgattcc tttctctgtg gttatctcat cctatgcgcg gattctggcc
481 actgtctacc atatgagctc tgtggaagga aggaagaaag cgtttgctac ctgctcgtct
541 cacatgactg tggtaacctt gttttatggg gctgccatat acacctatat ggtaccacac
601 tcttaccatt ccccatccca agacaaaatt ttttctgtgt tctataccat tctcacaccc
661 atgctgaac with a deduced amino acid sequence (SEQ ID NO:40)
SHLSFIDMMYISTIVPKMLVDYLLGQRTISFVGCTAQHFLYLTL

VGAEFFLLGLMAYDRYVAICNPLRYPVLMSRRICWIIIAGSWFGGSLDGFLLTPITMS

FPFCRSREINHFFCEAPAVLKLACADTALYETVMYVCCVLMLLIPFSVVISSYARILA

TVYHMSSVEGRKKAFATCSSHMTVVTLFYGAAIYTYMVPHSYHSPSQDKIFSVFYTIL

TPMLN (p)                                                        (SEQ ID NO:41)
  1 tgcaacttag cgaccatgga tattatctgc acctcctctg tactgcccaa ggcgctggtt
 61 ggtctactgt ctgaggaaaa caccatcccc ttcaaagggt gcatgactca gctcttcttt
121 cttgtgtggt ctggatcctc tgagctgctg ctgctcacag tcatggccta tgaccgctat
181 gtggccatct gtttgcccct gcattacagc tctaggatga gtccacagct ctgtgggacc
241 tttgccgtgg gtgtatggtc catctgcgca ctaaatgcat ctatcaacac tggtctgatg
301 acacggctgt cattctgtgg ccccaaggtc atcacccact tcttctgtga gattccccca
361 ctcctcctgc tctcctgtag tcctacatat ataaatagcg ttatgactct tgtggcagat
421 gccttttatg gaggcatcaa ttttttactt accttgctat cctatggctg catcattgcc
481 agcatcctgc gcatgcgttc tgctgagggc aagaggaagg ccttttctac ctgctcatcc
541 cacctcatcg tggtctctgt gtactactca tctgtgttct gtgcctatat cagtcctggt
601 tccagctaca gcccagaaag aagcaaattt acctcggttt tgtactcagt cctcagccca
661 accctcaac with a deduced amino acid sequence

```
CNLATMDIICTSSVLPKALVGLLSEENTIPFKGCMTQLFFLVWS                    (SEQ ID NO:42)
GSSELLLLTVMAYDRYVAICLPLHYSSRMSPQLCGTFAVGVWSICALNASINTGLMTR
LSFCGPKVITHFFCEIPPLLLLSCSPTYINSVMTLVADAFYGGINFLLTLLSYGCIIA
SILRMRSAEGKRKAFSTCSSHLIVVSVYYSSVFCAYISPGSSYSPERSKFTSVLYSVL
SPTLN
```

(q)
```
                                                                (SEQ ID NO:43)
  1 gccaacctct ccagtgtcga cattagtgct ccatctgtca ttgtccccaa ggcattggtg
 61 aatcatatgt tgggaagcaa gtccatctct tacacgggt gtatgaccca gatctatttc
121 ttcatcacat tcaacaatat ggatggcttc ctcctgagtg tgatggccta tgaccgctat
181 gtggccatct gtcaccctct ccactacacc atgatgatga acccagact ctgtgtcctc
241 ctggtggcca tatcatgggc catcacaaac ctgcatgctc tcttgcatac tctcctcatg
301 gttcgactca ccttctgttc ccacaatgca gtgcaccact tcttctgtga ccctacccct
361 atcctgaagc tctcttgttc tgacaccttc atcaatgacc tgatggtctt caccattggt
421 ggattggtat ttatgactcc atttacatgc attattgttt cctatgccta catcttctct
481 aaggttctga agttaaaatc tgcccatgga ataaggaaag ccctgtcgac gtgtgggtct
541 cacctcactg tggtctccct cttctatggg gcgatcctgg catctatat gcaccttca
601 tctacataca cagtgcagga cacagtggcc accgtcatct tcacagtagt gacacccatg
661 gtaaac accctcaac
``` with a deduced amino acid sequence

```
ANLSSVDISAPSVIVPKALVNHMLGSKSISYTGCMTQIYFFITF                    (SEQ ID NO:44)
NNMDGFLLSVMAYDRYVAICHPLHYTMMMRPRLCVLLVAISWAITNLHALLHTLLMVR
LTFCSHNAVHHFFCDPYPILKLSCSDTFINDLMVFTIGGLVFMTPFTCIIVSYAYIFS
KVLKLKSAHGIRKALSTCGSHLTVVSLFYGAILGIYMHPSSTYTVQDTVATVIFTVVT
PMVN
```

(r)
```
  1 agtcacttgg ccttcacgga catctctttc tcatctgtca cagctccaaa gatgctcatg   (SEQ ID NO:45)
 61 aatatgctga cacatagcca atccatctca catgctgggt gtgtttccca aatatatttt
121 ttcttattgt ttgggtgtat tgacaacttc cttctgactt ccatggccta tgacaggtat
181 gtggccatct gccaccctct gcattatacc actatcatga gtcaaagcct ctgtgttctg
241 ctagtgatgg tgtcctgggc attttcctct tctaatggcc ttgtgcatac tcttctcttt
301 gctcgtctct ctcttttag agacaacact gtccaccatt ttttctgtga tctctctgct
361 ttgctgaagc tgtccagctc agacactact atcaatgaac tagtaatcct cactttagca
421 gtggtggtca tcactgtacc attcatatgc atcctggttt cttatggcca catgggggcc
481 actatcctaa gaactccatc catcaagggt atctgcaaag ccttgtccac atgtggttct
541 catctctgtg tagtttcttt atattatgga gccattattg ggttatattt ttcccctcc
601 tccaataata ctaatgataa agatgtcata gtagctgtgt tgtacactgt ggttacaccc
661 atgctgaat accctcaac
``` with a deduced amino acid sequence

SHLAFTDISFSSVTAPKMLMNMLTHSQSISHAGCVSQIYFFLLF (SEQ ID NO:46)

GCIDNFLLTSMAYDRYVAICHPLHYTTIMSQSLCVLLVMVSWAFSSSNGLVHTLLFAR

LSLFRDNTVHHFFCDLSALLKLSSSDTTINELVILTLAVVVITVPFICILVSYGHMGA

TILRTPSIKGICKALSTCGSHLCVVSLYYGAIIGLYFFPSSNNTNDKDVIVAVLYTVV

TPMLN (s)

```
  1 atggcgaaca gcactactgt tactgagttt attttgctgg ggctgtcaga tgcctgtgag   (SEQ ID NO:47)
 61 ctgcaggtgc tcatattcct gggctttctc ctgacctact tcctcattct gctgggaaac
121 ttcctcatca tcttcatcac ccttgtggac aggcgccttt acaccccat gtattacttc
181 ctccgcaact tgccatgct ggagatctgg ttcacctctg tcatcttccc caagatgcta
241 accaacatca tcacaggaca taagaccatc tccctactag gttgtttcct ccaagcattc
301 ctctatttct tccttggcac cactgagttc tttctactgg cagtgatgtc ctttgacagg
361 tatgtggcca tttgtaaccc tttgcgttat gccaccatta tgagcaaaag agtctgtgtc
421 cagcttgtgt tttgctcatg gatgtctgga ttgcttctca tcatagttcc tagttcaatt
481 gtatttcagc agccattctg tggcccaaac atcattaatc atttcttctg tgacaacttt
541 ccacttatgg aactcatatg tgcagatact agcctggtag agttcctggg ttttgttatt
601 gccaatttca gcctcctggg cactctggct gtgactgcca cctgctatgg ccacattctc
661 tataccattc tacacattcc ttcagccaag gagaggaaga aagccttctc aacttgctcc
721 tctcatatta ttgtggtgtc tctcttctac ggcagctgta tcttcatgta tgtccggtct
781 ggcaagaatg gacaggggga ggatcataac aaggtggtgg cattgctcaa cactgtagtg
841 acacccacac tcaacccctt catctacact ctgaggaaca agcaggtgaa gcaggtattt
901 agggaacacg taagcaagtt ccaaaagttc agccagacgt gaaccctcaac
``` with a deduced amino acid sequence

MANSTTVTEFILLGLSDACELQVLIFLGFLLTYFLILLGNFLII (SEQ ID NO:48)

FITLVDRRLYTPMYYFLRNFAMLEIWFTSVIFPKMLTNIITGHKTISLLGCFLQAFLY

FFLGTTEFFLLAVMSFDRYVAICNPLRYATIMSKRVCVQLVFCSWMSGLLLIIVPSSI

VFQQPFCGPNIINHFFCDNFPLMELICADTSLVEFLGFVIANFSLLGTLAVTATCYGH

ILYTILHIPSAKERKKAFSTCSSHIIVVSLFYGSCIFMYVRSGKNGQGEDHNKVVALL

NTVVTPTLNPFIYTLRNKQVKQVFREHVSKFQKFSQT

Although each insert shared some sequence homology of previously characterized olfactory receptors, the sequenced receptors were all new members of the olfactory receptor family and were distributed broadly (shown in bold-type in FIG. 1B) across a similarity dendrogram. Also depicted in FIG. 1B are ten previously cloned olfactory receptors (see, e.g., Buck (1991) Cell 65:175–187), shown in italics in FIG. 1B, designated I3, I8, I14, I15, I9, F5, F3, F12, F6, and I7. Thus, the arrayed receptor plasmid inserts represented a diverse library of olfactory receptor sequences amenable to expression studies, described below.

Chimeric Vector Construction

PCR products were digested with PstI and BspEI restriction enzymes before size fractionation, purification and ligation into the pCMV-Rho/M4$_{NC}$ vector (see FIG. 1A). The vector ligation products were transformed into E. coli and 480 clones were placed in 96-well plates. PCR screening revealed that >95% of the clones carried inserts of the expected size. Pools of cells from a single column of the plates (8 wells) were grown in a 50 ml culture and plasmid DNA prepared. Insert-containing vectors containing: the 5'-untranslated region of the rhodopsin gene, which included its coding region for the initiation methionine and the next 19 residues; joined to a full-length cDNA for a mouse olfactory receptor (M4 or I-C6), under the control of the CMV promoter, were also prepared. The full-length coding region of olfactory receptors mI7 and I-C6 were obtained by screening a mouse (129 SV/J) genomic phage (λFIX-II) library ($2\times10^6$ independent clones) using $^{32}$P-labeled DNA fragments (of TMII through VII sequence) of the respective receptors under stringent conditions (hybridized at 0.2×SSC at 65° C.). DNA fragments encoding the full-length receptors were cloned into pBluescript (Stratagene) and sequenced.

Culture and Transient Transfection of Human Cells Expressing Olfactory Receptor

HEK-293 cells (obtained from the ATCC) were grown in DMEM supplemented with 10% fetal bovine serum, penicillin (100 U/ml), streptomycin (100 µg/ml) and L-glutamine (2 mM) in 5% $CO_2$. Before transfection, the cells were seeded onto poly-L-lysine-coated 10.5×35×0.17 mm glass coverslips (Bellco) placed in the 60 mm culture dishes. Calcium phosphate-mediated transfections were performed in a 60 mm dish with 3 to 4 µg of receptor construct DNA, 1 µg of pCIS Gα 15 and Gα16 expression vector (Offermanns (1995) supra). 2 µg of pBluescript carrier DNA, and 0.3 µg of pRSV-T antigen expression vector (Gorman (1990) DNA and Protein Eng. Tech. 2:3–9). After 5 to 7 hr incubation, the cells were washed once with PBS containing 0.5 mM EDTA and 10% DMSO, then with PBS before continuing growth in regular media for 40–50 hr.

Expression of Receptors on the Cell Surface for Functional Ligand-binding Assays Efficient screening of expressed olfactory receptors with a large number of ligands by functional analysis requires a robust and sensitive assay system. Although the established role of cAMP in olfactory signaling offers a biochemical approach involving measurement of cAMP production in response to odorant stimulation, an alternative, rapid assay is to co-express the cloned olfactory receptors with G protein $G\alpha_{15,16}$ subunits (see, e.g., Offermanns (1995) J. Biol. Chem. 270:15175–15180), which can promiscuously couple 7-transmembrane domain receptors that normally signal through other second messengers to the $PIP_2$ pathway. In this reporter system, (olfactory) receptor activation leads to the generation of an $IP_3$-mediated increase in intracellular $Ca^{2+}$, which can be measured at the single-cell level with high sensitivity and good temporal resolution using the dye FURA-2 and radiofluorometric imaging. These attributes were able to compensate for the low transfection efficiency in transient expression systems that would hinder more traditional biochemical assays.

A construct with the TM II–VII region from the $\beta_2$-adrenergic receptor inserted in the pCMV-Rho/M4$_{NC}$ vector (Rho/M4$_{NC}$-$\beta_2$ TM II–VII) was co-transfected with $G\alpha_{15,16}$ into HEK-293 cells. Immunocyto-chemical localization of vector-encoded, newly translated polypeptide with a B6-30 antibody against the rhodopsin tag (directed against the N-terminal 15 residues of rhodopsin, see Hargrave (1986 Exp. Eye Res. 42:363–373) was performed. Transfected HEK 293 cells were air dried and fixed in ice-cold methanol for 10 min. The fixed cells were blocked with 1.5% goat serum in PBS for 30 minutes and then incubated for 1 hour in PBS containing 0.03% goat serum and a 1:1000 dilution of the B6-30. After washing with PBS, a FITC-coupled, polyclonal anti-mouse antibody (Vector) was used to visualize the rhodopsin-tagged protein. Images of fluorescent cells were obtained on a Zeiss 510 confocal microscope with excitation at 488 nm. Results of the localization experiments indicated that a significant portion of the expressed protein appeared to be localized to the plasma membrane (10% or more of total expressed protein). These results demonstrate that the rhodopsin N-terminus-derived "translocation domain" of the invention, when expressed in the chimeric receptors, was the cause of the efficient translocation of the chimeric receptor molecules to the plasma membrane.

These transfected cells were then tested for their ability to functionally respond to ligand-receptor binding. The ligand, the adrenergic agonist isoproterenol, was "bath" applied to the transfected cells and single cell $Ca^{2+}$-imaging was performed. Cells were pre-loaded with the $Ca^{2+}$-sensitive fluorescent dye FURA-2 AM (Molecular Probes) by bathing in serum-free DMEM containing 4 µM of the membrane permeant chemical for 1 hr at 37° C., then washed with a standard bath solution (130 mM NaCl, 2 mM $CaCl_2$, 5 mM KCl, 10 mM glucose, 10 mM Na.HEPES/pH 7.4 at room temperature). For each experiment, a glass coverslip with FURA-2 loaded HEK 293 cells was introduced into an open-topped, longitudinal microperfusion chamber (300 µl bath volume mounted on a Zeiss Axiovert 135 microscope equipped with an F Fluar 40×/1.30 oil-immersion lens. The cells were superfused with test solutions typically for 30 to 40 seconds (5 ml/application) and washed out with 5 ml of bath solution at the end of each application. Each test solution was freshly diluted and manually applied with a micropipette into the chamber. Because of this manual procedure, there could be several seconds of delay in actual application from electronic tick marks used to define the beginning of application in each graph. At the same time, the solution flow might not be completely laminar. In most cases, the onset of Ca2+ rise in response to a specific solution occurred within 15 seconds of the beginning of solution application, though longer delays were sometimes observed. Acetylcholine was applied at the end of each experiment at 10 µM for 15–20 seconds. Ratiometric $Ca^{2+}$ measurements were performed as described by Grynkiewicz (1985) 260:3440–3450, with modifications using the Zeiss/Attofluor-Ratiovision imaging system. At 5-second intervals, the cells were sequentially illuminated for less than 100 ms, first at 340 nm and then at 380 nm. Fluorescence emission at 510 nm was monitored for each excitation wavelength via an intensified CCD camera. Averaged pixel intensities within 40 to 100 regions of interest, corresponding to 40 to 100 individual cells, were digitized and stored on a computer. Attofluor-Ratiovision software (Atto Instruments) was used to determine the $Ca^{2+}$-dependent fluorescence signal expressed as the $F_{340}/F_{380}$ ratio. Signals from all responding cells, or all cells (negative controls) were averaged and displayed as a function of time.

Isoproterenol bath application resulted in a transient increase in intracellular $Ca^{2+}$ in the transfected cells. The $Ca^{2+}$ transient induced by isoproterenol was dependent on cotransfection with the $G\alpha_{15,16}$ subunits. Cells transfected with the G protein subunits alone produced a small response to isoproterenol, presumably due to some endogenous β-adrenergic receptors on their surface. However, odorants such as heptanal (7-al) and octanal (8-al) had no effect.

A second application of isoproterenol frequently failed to elicit a response, possibly suggesting a rapid desensitization of the $G\alpha_{15,16}$-mediated signal transduction pathway. Although its mechanism is unclear, this rapid desensitization was a frequent observation with this expression system. HEK-293 cells have intrinsic muscarinic receptors coupled to the $PIP_2$ pathway via endogenous G proteins. The rise in intracellular $Ca^{2+}$ upon activation of this pathway by bath-applied acetylcholine (10 µM) served as a control in this system.

As a second test example, a Rho/M4$_{NC}$-ratI7 TM II–VII chimeric construct was generated and co-expressed with $G\alpha_{15,16}$ in HEK-293 cells. A $Ca^{2+}$ transient was observed in the transfected cells in response to 10 µM octanal. The transfected cell responded to 30 µM, but not 10 µM, of heptanal (a shorter aldehyde than octanal). The response to octanal also required the presence of $G\alpha_{15,16}$.

As with the $\beta_2$-adrenergic receptor, desensitization often occurred after a positive response. For example, little or no effect was observed upon a second application of octanal, even at 30 µM. A similar response profile was obtained with a construct in which the translocation domain of the invention (rhodopsin N-terminus) was fused to the full-length rat I7 odorant/ligand region encoding sequence. This chimeric receptor responded to octanal even at 1 µM. The ligand specificity was not absolute; a small response was also observed to 30 µM heptanal (similar to an in vivo finding by Zhao (1998) Science 279:237–242). Sometimes, the delay between the start of odorant application and the beginning of $Ca^{2+}$ rise could be more than 30 seconds (e.g., the first response to octanal). The reason for this relatively long delay is unknown, but it could have arisen from a non-linear, thresholding mechanism. Additional experiments in which successive applications of two odorants were separated by periods as long as 5 minutes, however, removed any possible confusion with respect to which odorant triggered a given response.

The above results validate the HEK-293 cell expression of cloned olfactory receptor sequences as a screening system for identifying unknown odorants. They also demonstrate that odorant/ligands are binding to the 7-transmembrane domain region TM II–VII of an olfactory receptor to produce a physiologic response (in these experiments, measured by $Ca^{2+}$ transients).

Identification of Cognate Ligand-receptor Pairs for the Cloned Receptor Library

The 7-transmembrane domain region TM II–VII expressing vector libraries of the invention were expressed in this cell expression system. Various odorant were screened for their ability to generate a physiologic response in the form of a calcium transient, as above. Eighty plasmid clones arrayed in microtiter plates were pooled into 10 groups of eight constructs each, and co-transfected with $G\alpha_{15,16}$ into HEK-293 cells. After pre-loading with FURA-2, the transfected cells were screened sequentially against each of 26 odorants: Hedione, (–) carvone, (+) carvone, (+) citronellal, (–) citronellal, 2-methyl-4-propyl-1,3-oxalthiane, methylsalicylate, pyrrolidine, quinoleine, lyral, cyclohexanone, acetophenone, 2-methoxy-3-methyl-pyrazine, pyrazine, 2-methoxypyrazine, isovaleric acid, isobutyric acid, triethylamine, citralva, (+) limonene, 6-aldehyde, 7-aldehyde, 8-aldehyde, 9-aldehyde, 10-aldehyde, and 11-aldehyde (Firmenich, S. A., Princeton, N.J.). The odorants were stored under nitrogen. Stock solutions of the odorants were made up fresh each day in DMSO and diluted 1000-fold into the standard bath solution to give the indicated concentrations approximately 10 seconds before application in a given experiment.

All of the (twenty-six) odorants were applied at 10 µM to induce a $Ca^{2+}$ response as described previously. Three sample "pools" (a mixture of clones) produced transient increases in $Ca^{2+}$ in response to the application of (–) carvone, (–) citronellal and (+) limonene, respectively. The lack of response of one pool to (+) carvone could reflect desensitization resulting from the positive response to (–) carvone occurring immediately before, or, alternatively, a stereo-specificity in ligand recognition. This desensitization could also have obscured the response to subsequent odorant applications; nonetheless, a second response to (–) carvone could still be elicited. The absence of response to (+) citronellal for another pool apparently results from a genuine stereo-specificity in ligand recognition, because there was no prior positive response that would lead to desensitization. The lack of responses to the subsequent odorants was confirmed by additional experiments with the same set of odorants but (–) where citronellal was applied last.

Next, 8 individual clones from each of these three tested pools were isolated and tested for their ability to encode receptor binding domains with specificity for the odorants identified above. Three responsive chimeric olfactory receptors were isolated; they were designated I-D3 (carvone), I-C6 (citronellal) and I-G7 (limonene). Further experiments indicated that the I-D3 receptor was responsive to both (+) and (–) carvone). The I-C6 receptor appeared to be selective for the (–) stereoisomer of citronellal. Finally, the I-G7 receptor responded to both (+) and (–) limonene at the same concentration of 10 µM, though perhaps not as well to the (–) isomer. For each of the three isolates, control experiments indicated that the specific responses required the presence of $G\alpha_{15,16}$ (as discussed above).

To determine if these physiologic responses were caused by ligand interaction with a full-length 7-membrane receptor, a genomic clone of the entire I-C6 receptor coding sequence was isolated and used to make a chimeric molecule incorporating the tranlocation domain of the invention (the "rhodopsin tag" sequence). The full-length I-C6 receptor retained the same stereo-selectivity as a chimeric receptor construct whose only I-C6 sequence was the transmembrane domains II through VII (i.e., the odorant/ligand binding domain). Both recombinantly expressed receptors preferred the (–) isomer of citronellal; it also showed high sensitivity, responding to this chemical even at 1 µM. The stereo-specificity was not absolute, however, in that (+) citronellal was also able to elicit a response when applied at 30 µM and 100 µM. By comparison, carvone and limonene elicited no responses from this receptor even at 100 µM. Five structurally related compounds besides (–) and (+) citronellal were also tested (+/– citral, (–) citronellyl bromide, (–) citral demethyl acetal, (–) citronellic acid and (–) citronellol), all at 30 µM. Among these, only 30 µM (–) citronellyl bromide elicited a small response. This compound differs from (–) citronellal by the substitution of a bromine for the oxygen atom in the aldehyde functional group. The lack of response to (–) citronellal may be due to desensitization resulting from the positive response to 30 µM (+) citronellal immediately before. Finally, in control experiments lacking $G\alpha_{15,16}$, no response was observed to either (–) citronellal or (–) citronellyl bromide (FIG. 5C). Although these experiments do not quantitate ligand affinities, they provide a qualitative rank order of potency for binding and activating the I-C6 receptor: (–)citronellal>(+)citronellal, citronellyl bromide>28 other odorants.

Analysis of Individual Amino Acid Residues on Receptor-odorant Binding Specificities To establish the functional expression of mouse olfactory receptors, a Rho/M4$_{NC}$-mouse I7 transmembrane II–VII chimeric receptor was constructed and examined its responsiveness to several n-aliphatic aldehydes and alcohols. At 10 µM concentrations of these odorants, the mouse receptor responded only to heptanal. As discussed above, the rat I7 chimeric receptor responded better to octanal than to heptanal in identical experiments. This difference in odorant selectivity was retained by the full-length clones of the two receptors fused to the translocation domain of the invention (the rhodopsin tag). The rat and mouse I7 receptors differ in altogether 15 amino-acid residues, three of which ($K_{90}E$ in the $1^{st}$ extracellular loop, $V_{206}I$ in TM V, and $F_{290}L$ in TM VII) reside between transmembrane domains II and VII.

In light of the critical role of residues in transmembrane V for ligand binding in the $\beta_2$-adrenergic receptor, the role of residue 206 in differential ligand recognition was examined. Reciprocal valine/isoleucine substitutions were made in the full-length rat and mouse I7 receptor sequences. These substitutions were able to switch the ligand preferences of the two receptors, namely, making the rat I7 receptor preferentially recognize heptanal and the mouse receptor preferentially recognize octanal. Interestingly, the nature of these changes, isoleucine versus valine and heptanal versus octanal, is consistent with compensatory alterations in the structures of ligand and receptor that preserve the complementarity between the two. These observations provide strong evidence for a direct role of residue 206 in the interaction between the I7 receptor and aliphatic aldehydes. These results also demonstrate that the compositions and methods of the invention can be used to analyze odorant/ligand-olfactory receptor interactions on a molecular level.

Summary

The few studies carried out previously on identifying cognate odorant-olfactory receptor pairs have generally focused on a single receptor and examined its responsiveness to a large number of odorants or odorant mixtures. The present invention provides the means to take a different approach by generating olfactory receptor libraries to use in the screening of a large number of cloned receptors simultaneously against a large panel of individual odorants. In this way, the problem of poor expression, inefficient folding or weak coupling to second-messenger systems associated with certain receptors in a heterologous system is avoided. Moreover, screening multiple receptors against multiple odorants, greatly increases the probability of identifying responsive combinations of receptors and odorants. Finally, the apparent diversity of the receptor sequences should further enhance the scan of the odor space. The above-described experiments screened 80 clones (not counting the I7 receptor) against 26 odorants. Because a given odorant should be recognized by at least one member of, say, a total of 1000 receptors, the chance of encountering an odorant that is a cognate ligand to 80 receptors should, on average, be 8% (=80/1000), or 2 positives in a pool of 26 odorants. This number is close to the number (3) identified experimentally herein. The receptor library generated with a single pair of degenerate primers of the invention (the TM II to TM VII amplifying pair) encompasses a broad range of the olfactory receptor family. Several hundred distinct sequences are represented in this exemplary library of the invention.

The addition of translocation domains of the invention (the first twenty amino-acid residues of a rhodopsin N-terminal segment, with some exemplary domains also consisting of a 5'-untranslated rhodopsin region) to the chimeric olfactory receptors of the invention facilitated their plasma membrane localization. This included the full-length I-C6 receptor, where the inclusion of the translocation domain was necessary in order to observe a response to (−) citronellal. The different translocation domains of the invention may be aiding in the translocation process in different ways; however, the invention is not limited by what structural contribution may be played by the translocation domain to the newly translated protein's translocation process.

What is claimed is:

1. A method of determining whether a test compound binds to a mammalian olfactory receptor comprising the following steps:
   (i). expressing a nucleic acid under conditions permissive for translation of the nucleic acid to a receptor polypeptide, wherein the nucleic acid encodes a 7-transmembrane polypeptide that can transverse a plasma membrane seven times and wherein the nucleic acid comprises the following domains in 5' to 3' order:
   a nucleic acid encoding an amino terminal plasma membrane translocation domain as shown in SEQ ID NO: 3;
   a nucleic acid encoding a first transmembrane domain as shown in residues 2 1–79 of SEQ ID NO: 55; and
   a nucleic acid encoding an olfactory receptor ligand-binding region as shown in SEQ ID NO: 48;
   (ii). contacting the translated polypeptide with the test compound; and
   (iii). determining whether the test compound binds to the polypeptide.

2. A method of determining whether a test compound binds to a mammalian olfactory transmembrane receptor comprising the following steps:
   (i). culturing a cell stably or transiently transfected with a chimeric nucleic acid which encodes a 7-transmembrane polypeptide that can transverse a plasma membrane seven times, said chimeric nucleic acid comprising a first, second, and third nucleic acid sequence in 5' to 3' order:
   a first nucleic acid sequence encoding an amino terminal plasma membrane translocation domain as shown in SEQ ID NO: 3;

a second nucleic acid sequence encoding a first transmembrane domain as shown in residues 21–79 of SEQ ID NO: 55; and a third nucleic acid sequence encoding an olfactory receptor ligand-binding region as shown in SEQ ID NO: 48;

under conditions permissive for translation of the nucleic acid to form a 7-transmembrane polypeptide on the cell's plasma membrane outer surface;

(ii). contacting the cell with the test compound; and (iii). determining whether the test compound binds to the 7-transmembrane polypeptide.

3. The method of claim 2, wherein the binding of the test compound to the 7-transmembrane polypeptide is determined by measuring a change in the physiologic activity of the cell, wherein a change in the cell's activity measured in the presence of the test compound compared to the cell's activity in the absence of the test compound provides a determination that the test compound binds to the 7-transmembrane polypeptide.

4. The method of claim 3, wherein the measured cell activity is a change in the calcium ion ($Ca^{2+}$) or cAMP concentration in the cell.

5. The method of claim 4, wherein the calcium ion concentration is measured by loading the cell with a calcium ion-sensitive fluorescent dye before contacting the cell with the test compound.

6. The method of claim 2, wherein the cell is a human cell or a *Xenopus* oocyte.

* * * * *